(12) United States Patent
Kuno et al.

(10) Patent No.: US 6,630,293 B1
(45) Date of Patent: Oct. 7, 2003

(54) METHOD FOR PRODUCING SILVER SALT OF ORGANIC ACID AND PHOTOTHERMOGRAPHIC MATERIAL UTILIZING THE SAME

(75) Inventors: Koichi Kuno, Minami-ashigara (JP); Naoyuki Kawanishi, Minami-ashigara (JP); Yoichi Nagai, Odawara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/692,718

(22) Filed: Oct. 20, 2000

(30) Foreign Application Priority Data

Oct. 20, 1999 (JP) .............................. 11/297964
Mar. 29, 2000 (JP) ........................... 2000/090093

(51) Int. Cl.$^7$ .............................. G03C 1/005; G03C 1/38
(52) U.S. Cl. ........................................ 430/620; 430/631
(58) Field of Search ................................. 430/620, 619, 430/631

(56) References Cited

FOREIGN PATENT DOCUMENTS

| EP | 0754969 | A2 | 1/1997 |
| EP | 0848286 | A1 | 6/1998 |
| EP | 0848286 |  * | 6/1998 |
| EP | 0962814 | A1 | 12/1999 |
| EP | 0962815 | A1 | 12/1999 |

* cited by examiner

Primary Examiner—Thorl Chea
(74) Attorney, Agent, or Firm—Birch, Stewart, Kolasch & Birch, LLP

(57) ABSTRACT

A method for producing a silver salt of an organic acid, which comprises steps of reacting (1) a solution containing silver ions in water or in a mixture of an organic solvent and water, with (2) a solution or suspension containing an alkali metal salt of an organic acid in water, in a mixture of an organic solvent and water, or in an organic solvent to prepare a silver salt of an organic acid, and removing a byproduct salt by a desalting operation, wherein a dispersing agent having a molecular weight of 3000 or less is added and dispersed during a time period of from before the reaction to before the desalting operation. There is provided a method for producing a silver salt of an organic acid, which can provides low fog, high sensitivity and high concentration of blackening when it is used for photothermographic materials, and is suitable for the production of photothermographic materials having low haze and less image degradation after storage.

17 Claims, 1 Drawing Sheet

METHOD FOR PRODUCING SILVER SALT OF ORGANIC ACID AND PHOTOTHERMOGRAPHIC MATERIAL UTILIZING THE SAME

FIELD OF THE INVENTION

The present invention relates to a method for producing a silver salt of an organic acid and a photothermographic material utilizing the silver salt.

BACKGROUND OF THE INVENTION

In recent years, reduction of amount of waste processing solutions is strongly desired in the medical field from standpoints of environmental protection and space savings. Techniques relating to photosensitive thermographic materials for use in the medical field and photographic-art processes are required which enables efficient exposure by a laser image setter or a laser imager and formation of a clear black image having high resolution and sharpness. The photosensitive thermographic materials can provide users with a more simple and non-polluting heat development processing system that eliminates the use of solution-type processing chemicals.

The same need applies to the field of ordinary image-forming materials. However, photo-images for medical use require high quality excellent in sharpness and graininess as they need very fine images. In addition, for easy diagnosis, cold monochromatic images are preferred. At present, various types of hard copy systems using pigments and dyes, for example, ink jet printers and electrophotographic systems are available as ordinary image forming systems. However, no satisfactory system is available for medical use.

Methods utilizing a silver salt of an organic acid for forming an image by heat development are described, for example, in U.S. Pat. Nos. 3,152,904 and 3,457,075 and Klostervoer, "Thermally Processed Silver Systems", Imaging Processes and Materials, Neblette, 8th ed., compiled by J. Sturge, V. Walworth and A. Shepp, Chapter 9, p.279, (1989). Generally, the phototlhermographic material, in particular, comprises a image-forming layer (photosensitive layer) containing a photocatalyst (e.g., silver halide) in a catalytically active amount, a reducing agent, a reducible silver salt (e.g., silver salt of an organic acid), and optionally a toning agent for controlling tone of silver, which are usually dispersed in a binder matrix. When the photothermographic material is heated at a high temperature (e.g., 80° C. or higher) after light exposure, a monochromatic black silver image is produced through an oxidation-reduction reaction between the silver halide or the reducible silver salt (which functions as an oxidizing agent) and the reducing agent. The oxidation-reduction reaction is accelerated by catalytic action of a latent image of silver halide generated upon exposure. Therefore, the monochromatic silver images are formed in exposed areas of the materials. This technique is disclosed in many references including U.S. Pat. No. 2,910,377 and Japanese Patent Publication (Kokoku, hereinafter referred to as JP-B) 43-4924. The photothermographic systems using a silver salt of an organic acid can achieve image quality and tones that satisfy the needs in the medical filed.

The silver source used in these systems is generally a silver salt of a fatty acid, and various methods for producing the same are known. Examples of the methods include a method of preparing a silver salt of an organic acid under coexistence of water and a hardly water-soluble solvent as disclosed in Japanese Patent Laid-open Publication (Kokai, hereinafter referred to as JP-A) 49-93310, JP-A-49-94619 and JP-A-53-68702, a method of preparing a silver salt of an organic acid in an aqueous solution as disclosed in JP-A-53-31611, JP-A-54-4117 and JP-A-54-46709, a method of preparing a silver salt of an organic acid in an organic solvent as disclosed in JP-A-57-186745, JP-A-47-9432 and U.S. Pat. No. 3,700,458 and so forth. Basically, the preparation is carried out by heating a fatty acid to a temperature higher than melting point thereof to dissolve the acid in water, adding sodium hydroxide or an alkali metal salt with vigorous stirring, and then adding silver nitrate to convert the alkali soap into silver soap.

Such alkali soap forms micelles in an aqueous solution, and gives a solution of whitely turbid appearance. The reaction from such a micelle state to the silver soap often suffers from problems concerning production stability. Therefore, as a method for obtaining the alkali soap as a uniform solution, a method of using a mixed solution of water and alcohol as the solvent is disclosed in JP-A-55-40607.

Further, alkali soap presents alkalinity as indicated by its name. Therefore, the silver soap will be prepared under a high pH condition in the above method. However, addition of a solution containing silver ions into an alkaline solution not only produces silver oxide as a byproduct, but generates unintended silver nuclei produced by a trace amount of reducing contaminants, which are unavoidable in a production process and exhibit high reducing property due to the high pH. Such byproducts are highly disadvantageous since they degrade performance of photothermographic materials, in particular, cause undesired fog. The problem of fog is not solved even by the method disclosed in JP-A-55-40607, which aims at obtaining a uniform solution to suppress generation of the byproducts.

In addition, JP-A-9-127643 discloses a method for producing a silver salt by simultaneous addition of measured amounts of an alkali metal salt solution and a silver nitrate solution, and the reference describes simultaneous addition of a solution of sodium behenate in a mixture of water and isopropyl alcohol and a solution of silver nitrate. This method can at least lower the high pH of the reaction to a neutral region, and thus is preferred to reduce the generation amount of silver oxide. However, isopropyl alcohol has weak reducing property, which makes the method insufficient to completely solve the problem of fog.

Moreover, the silver behenate grains formed by this method are two-dimensionally and anisotropically grown acicular grains having a size of 0.04 $\mu$m to 0.05 $\mu$m, and the reference contains no description concerning control of the grain size or grain shape.

In order to obtain a uniform dispersion practically usable as a coating solution containing a silver salt of an organic acid, it is necessary to achieve a state in which the silver salt of an organic acid is finely dispersed in a solvent without aggregation. For this reason, it is necessary to develop a method for dispersing the silver salt of an organic acid as fine grains. An ordinarily used method includes a method comprising the steps of separating the formed hydrophobic grains of silver salt of an organic acid as solid by filtration, mixing a dispersing agent with the solid and re-dispersing the mixture as described by Kloosterboer (Imaging Processes and Materials, Noblette, 8th ed., compiled by J. Sturge, V. Walworth and A. Shepp, Chapter 9, p.279, (1989)).

As the method for dispersing a silver salt of an organic acid as fine grains, a method of mechanically dispersing the salt in the presence of a dispersing aid by a known pulverization means (e.g., high-speed mixer, homogenizer, high-speed impact mill, Banbary mixer, homomixer, kneader, ball mill, vibrating ball mill, planetary ball mill, attriter, sand mill, bead mill, colloid mill, jet mill, roller mill, trone mill and high-speed stone mill). However, these methods only produce a coating solution containing a lot of aggregated particles, i.e., a coating solution that gives bad coated surface quality, as well as they cause a, problem that, because the methods possibly grind primary grains of a silver salt of an organic salt originally crystallized as a hardly wafer-soluble salt without any selectivity, silver nuclei are formed at crystal cleavage surfaces and causes increase of fog.

Several methods have been proposed, wherein the primary grains obtained during the reaction of a solution of alkali metal salt and a solution containing silver ions are utilized as they are, not separating the silver salt of an organic acid as solid and finely dispersing the solid.

For example, JP-A-8-234358 discloses a method of adding silver nitrate to an aqueous dispersion in which fine grains of an alkali salt of an organic acid are dispersed, and desalting the obtained dispersion of a silver salt of an organic acid by ultrafiltration. This method further utilizes means for enhancing dispersion stability by carrying out the ultrafiltration by adding beforehand with water-soluble protective colloids such as polyvinyl alcohol and gelatin.

However, the shape of the silver salt of an organic acid obtained by this method is limited to an acicular shape, and in addition, it is difficult to control the grain size. Therefore, the method is still insufficient to stably achieve performance of low fog, high blackening density and low haze, which are desired for photothermographic materials.

JP-A-9-127643 discloses a method of directly desalting dispersion of silver salt of an organic acid obtained by simultaneous addition of measured amounts of solution of an alkali-metal salt and a silver nitrate solution by means of dialysis or ultrafiltration. In this method, primary grains obtained during the crystallization of the silver salt of an organic acid can be introduced into photosensitive layer without degrading the grains. However, problems of aggregation of grains under a condition of high salt concentration, an increase of viscosity upon concentration of the dispersion and so forth are not solved,;and thus this method is still insufficient as practical means for obtaining a uniform dispersion.

JP-A-9-127643 discloses a method of co-using a dispersing agent, similar to the method of JP-A-8-234358. However, the references contain no description of kinds of preferred dispersing agents. This method fails to provide superior dispersion stability, because the grain shape and the size are controlled in the presence of high salt concentration during generation of grains of silver salt of an organic acid and under co-existence of an organic solvent such as isopropyl alcohol.

In order to obtain fine and mono-dispersed grains of a silver salt of an organic acid, vigorous stirring is required during addition of an alkali metal salt solution and a solution containing silver ions. In particular, the solution of an organic acid alkali metal salt dissolved at a high temperature suffers from rapid temperature decrease to form precipitations upon addition thereof, and therefore large grains may grow if dilution rate or fluidization is slow or weak. When they are added to a tank in which a gas/liquid interface is present, and the stirring speed is increased, entrainment of air is caused. The grains of silver salt of organic acid are highly hydrophobic, and therefore the grains are adsorbed on the surfaces of the entrained bubbles to stabilize the bubbles and prevent breakage thereof, and in addition, the adjacent grains on the bubbles are aggregated. The liquid containing air entrained in such a manner becomes a whipped cream-like liquid of high viscosity, and disturbs uniform reaction.

Further, if the liquid temperature is still high after the reaction of the silver ion solution and the alkali metal salt solution, the grains grow due to physical ripening. Therefore, the liquid temperature is preferably maintained at around room temperature. Whilst, in order to obtain a stable solution of alkali metal salt of a long-chain fatty acid, it is necessary to maintain a high temperature of 50° C. or more. Therefore, it is necessary to quickly obtain heat exchange for offsetting the heat introduced by the added solution. For example, in a method using a tank or the like provided with a jacket tank, when the concentration of dispersion produced from the reaction becomes high, fluidity of the liquid is disturbed and hence sufficient heat exchange cannot be achieved. Therefore, scaling up of the reaction and reaction in a concentrated liquid system are obstructed.

As described above, no method has been known so far which enables stable production of monodispersed silver salt of an organic acid with low fog, and independent control of the grain size and the grain shape.

SUMMARY OF THE INVENTION

An object of the present invention is to provide a method for producing silver salt of an organic acid, which solves the aforementioned problems. More specifically, the object is to provide a method for producing a silver salt of an organic acid, which can freely control the grain shape and grain size, and is suitable for scaling up or utilizing more concentrated solutions.

Another object of the present invention is to provide a photothermographic material having low fog and high sensitivity, and high blackening density, as well as having low haze and less image degradation after development, when it is used as a photothermographic material.

A further object of the present,invention is to provide a photothermographic material having good silver tone and photographic properties upon development and superior stability before and after light exposure and development.

The inventors of the present invention conducted extensive studies to achieve the aforementioned objects. As a result, they found that the aforementioned objects could be achieved by the characteristics mentioned below and achieved the present invention.

The present invention thus provides a method for producing a silver salt of an organic acid, which comprises the steps of reacting (1) a solution containing silver ions in water or a mixture of an organic solvent and water, with (2) a solution or a suspension containing an alkali metal salt of an organic acid in water, a mixture of an organic solvent and water, or an organic solvent to prepare a silver salt of an organic acid, and removing byproduct salt by a desalting operation, wherein a dispersing agent having a molecular weight of 3,000 or less is added and dispersed during the period ranging from before the reaction to before the desalting operation.

As preferred embodiments of the aforementioned method, there are provided the aforementioned method, which further comprises a step of adding a dispersing agent having a molecular weight of more than 3000 after completion of the reaction of the silver salt of an organic acid and before completion of the desalting operation; the aforementioned method, wherein the dispersing agent having a molecular weight of more than 3000 is a nonionic surfactant; the aforementioned method, wherein the desalting operation is carried out by ultrafiltration; the aforementioned method, wherein the dispersing agent having a molecular weight of 3000 or less is an ionic surfactant that has anionic nature and has a hydrophobic group having 8 to 40 carbon atoms; the aforementioned method, wherein the desalting operation is carried out by ultrafiltration, and a ultrafiltration membrane used has a fractional molecular weight 10 to 50 times as much as the molecular weight of the ionic surfactant; the aforementioned method, wherein the desalting operation is carried out by ultrafiltration, and a ultrafiltration membrane used provides 0 to 50% of rejection against the ionic surfactant; and the aforementioned method, wherein the dispersing agent having a molecular weight of more than 3000 has a molecular weight 5 to 50 times as much as the fractional molecular weight of the ultrafiltration membrane.

As one of preferred embodiments of the present invention, there is provided a method for producing a silver salt of an organic acid, wherein (1) a solution containing silver ions in water or a mixture of an organic solvent and water, and (2) a solution or suspension containing an alkali metal salt of an organic acid in water, a mixture of an organic solvent and water, or an organic solvent are reacted to form grains of silver salt of an organic acid, (3) at least one surfactant having anionic nature and a hydrophobic group having 8 to 40 carbon atoms is added to a reaction mixture during a period ranging from before start of the reaction to before the desalting operation, and a macromolecular dispersing agent having a molecular weight 5 to 50 times as much as the fractional molecular weight of a ultrafiltration membrane used in the following step is added, and (4) a byproduct salt is removed by ultrafiltration using a membrane having a fractional molecular weight 10 to 50 times as much as the molecular weight of the ionic surfactant, or (b) a byproduct salt is removed by ultrafiltration using a membrane achieving 0 to 50% of rejection against the ionic surfactant, or (c) a byproduct salt is removed by a combination of the operations of (a) and (b).

As preferred embodiments of the present invention, there are further provided the aforementioned method, wherein a concentration of the ionic surfactant is 5 to 100 times the critical micelle concentration of surfactant; the aforementioned method, wherein the ionic surfactant is added before completion of the addition of the solution containing silver ions; the aforementioned method, wherein a hydrophilic group of the ionic surfactant is sulfonic acid or a sulfuric acid ester salt having at least one aromatic group; the aforementioned method, which comprises a step of supplementing the ionic surfactant so:that the ionic surfactant concentration is kept constant during the desalting operation by ultrafiltration; the aforementioned method, which comprises a step of carrying out the desalting operation by ultrafiltration while supplementing a different ionic surfactant; the aforementioned method, wherein the ultrafiltration operation is performed prior to the addition of the nonionic macromolecular dispersing agent, andiconductivity of the organic acid silver salt dispersion is less than 2000µS/cm when the nonionic macromolecular dispersing agent is added; the aforementioned method, wherein 2- to 10-fold constant volume dilution is performed after the addition of the nonionic macromolecular dispersing agent; the aforementioned method, wherein the concentration of the nonionic macromolecular dispersing agent is 0.1 to 30% by weight of the solid content of the silver salt of an organic acid; the aforementioned method, wherein the nonionic macromolecular is any one of polyvinyl alcohol, polyvinylpyrrolidone, or hydroxypropylcellulose, or a combination thereof; and the aforementioned method, which comprises a step of concentrating the dispersion to a concentration of 10% to 50% by weight after the constant volume dilution is performed.

In the presence of the ionic surfactant having anionic nature and a hydrophobic group having 8–40 carbon atoms, interfacial tension of the solid/liquid interface, selective adsorption to crystal surfaces of the silver salt of an organic acid and so forth can be controlled while the alkali metal salt of an organic acid and the silver ions are reacted to form grains of silver salt of an organic acid. Therefore, it becomes possible to selectively produce grains of any one of various shapes such as acicular shape, rod-like shape, scaly shape and tabular shape. In addition, the grain size and the grain size distribution can be readily controlled based on the aforementioned characteristics together with the defined mixing or temperature during the reaction. Furthermore, a dispersion obtained as described above will have a lower viscosity compared with a dispersion prepared without using the aforementioned surfactant, and therefore ease of stirring and mixing, heat exchange efficiency, handling property of the liquid and so forth are improved. Thus, the method is industrially advantageous as a production method having superior aptitude for manufacturing process and suitability for scaling up.

As the surfactant to be used, an anionic surfactant is preferred from viewpoints of solubility, adsorptivity to grains of silver salt of an organic acid and so forth. However, when an anionic surfactant is finally contained in a photothermographic material, hygroscopicity of the photosensitive material may become high due to its ionic nature, and it may sometimes adversely affect sensitivity and gradation, as well as color tone and image storability. In a preferred embodiment of the present invention, ad photothermographic material excellent in the total performance can be provided by replacing a low molecular weight dispersing agent, in particular, an ionic surfactant having anionic nature and a hydrophobic group having 8 to 40 carbon atoms, which adversely affects the performance of the photothermographic material although it is preferred for the formation of silver salt of an organic acid during the ultrafiltration operation, with a macromolecular dispersing agent of low hygroscopicity, in particular, a nonionic macromolecular dispersing agent.

As another aspect, there is provided a method for producing a photothermographic material containing a photosensitive silver halide, a silver salt of an organic acid, a reducing agent for silver ions and a binder on at least one side of a support, wherein the silver salt of an organic acid prepared by the aforementioned method is used. As a preferred embodiment of the method, there is provided the aforementioned method, wherein a binder of an image-forming layer containing the photosensitive silver halide and the silver salt of an organic acid is composed of a polymer having an equilibrium moisture content of 2% by weight or less at 25° C. and 60% relative humidity, and the method comprises a step of coating the image-forming layer by using a coating solution containing 30% by weight or more of water in the solvent of the solution. Further, there is also provided a photothermographic material produced by the aforementioned method.

According to the method of the present invention, undesired byproduct inorganic salts or organic solvent used in the reaction can be removed without extracting the reacted silver salt of an organic acid as a solid and re-dispersing the same, and therefore the productivity is markedly improved. Further, by using the silver salt of an organic acid, there can be provided a photothermographic material having low fog, high sensitivity, and high density of blackening, as well as having low haze and less image degradation after storage. This photothermographic material is characterized in that it provides good silver color tone and photographic properties upon heat development, and the material is stable before and after the light exposure and development.

PREFERRED EMBODIMENT OF THE INVENTION

Figure 1:
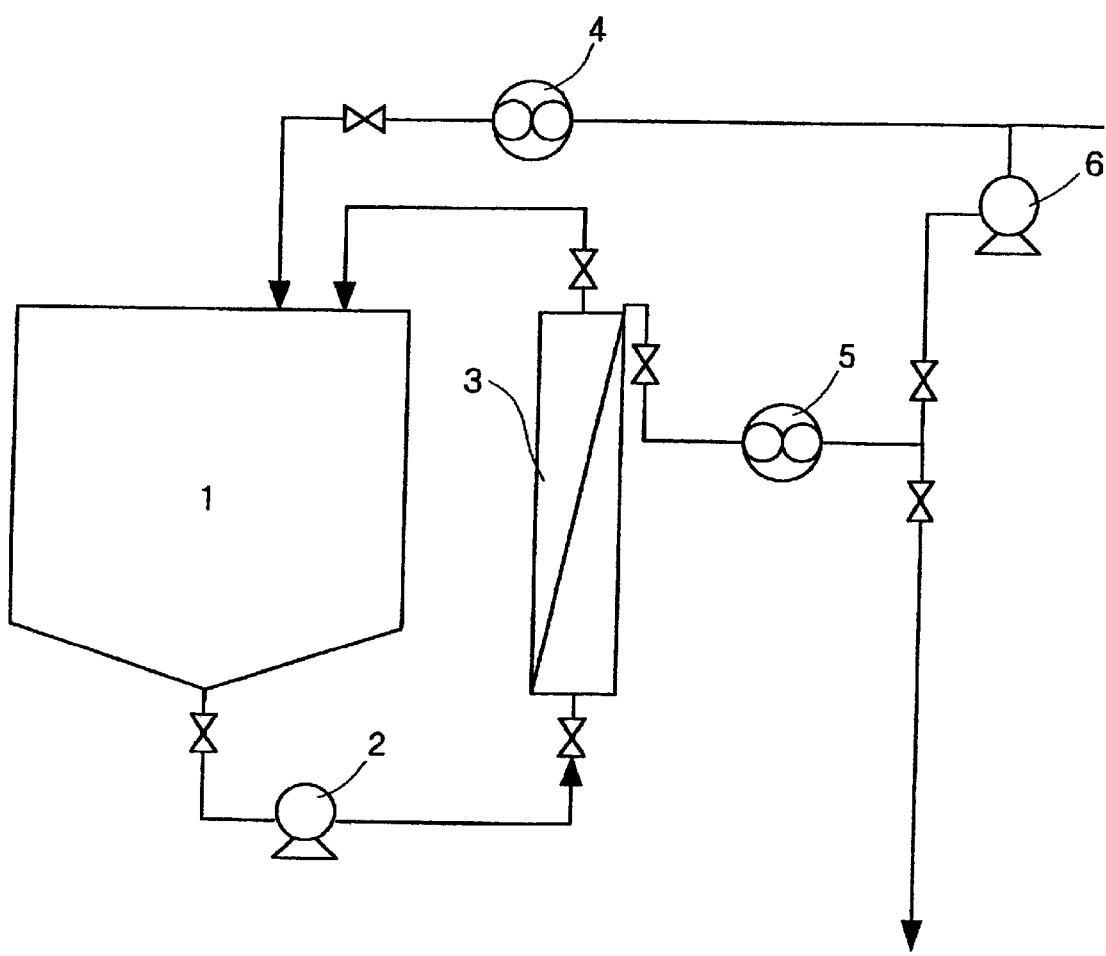
FIG. 1 shows an exemplary design of an apparatus used for ultrafiltration treatment. The apparatus comprises a tank 1, a circulation pump 2, an ultrafiltration module 3, a flowmeter 4 for measuring supplemental pure water, a flowmeter 5 for measuring permeated water, and a pump 6 for washing in reverse direction.

A silver salt of an organic acid that can be used in the present invention is a silver salt relatively stable against light, but forms a silver image when it is heated at 80° C. or higher in the presence of an exposed photocatalyst (e.g., a latent image of photosensitive silver halide) and a reducing agent. The silver salt of an organic acid may be any organic substance containing a source capable of reducing the silver ion. Such non-photosensitive silver salts of an organic acid are disclosed in JP-A-10-62899, paragraphs 0048 to 0049 and EP 0803763A1, page 18, line 24 to page 19, line 37. Silver salts of a long-chain aliphatic carboxylic acid having from 10 to 30, preferably from 15 to 28 carbon atoms are particularly preferred. Preferred examples of the organic acid silver salt include silver behenate, silver arachidinate, silver stearate, silver oleate, silver laurate, silver caproate, silver myristate, silver palmitate, mixtures thereof and so forth.

The shape of the silver salt of an organic acid that can be used for the present invention is not particularly limited. Scaly silver salts of an organic acid are preferred for the present invention. Scaly silver salts of an organic acid are herein defined as follows. A sample of a silver salt of an organic acid is observed under an electronic microscope, and the shape of the observed grains of the salt of an organic acid is approximated to rectangular parallelepiped. The edges of each rectangular parallelepiped are named as a, b and c according to increasing size (c and b may be the same). From the shorter edges a and b, x is obtained according to the following equation:

$$x = b/a$$

The values of x are obtained for about 200 grains, and an average of the value is named as x (average). Samples that satisfy the requirement of x (average) $\geq 1.5$ are defined to be scaly. Scaly grains preferably satisfy $30 \geq x$ (average) $\geq 1.5$, more preferably $20 \geq x$ (average) $\geq 2.0$. Acicular grains satisfy $1 \leq x$ (average) $\leq 1.5$.

In scaly grains, "a" is interpreted as the thickness of tabular grains of which main planes are defined by the sides of b and c. The average of "a" is preferably from 0.01 μm to 0.23 μm, more preferably from 0.1 μm to 0.20 μm. The average of c/b is preferably from 1 to 6, more preferably from 1.05 to 4, most preferably from 1.1 to 3, most preferably from 1.1 to 2.

The grain size distribution of the silver salt of an organic acid is preferably monodisperse. The term "monodisperse" as used herein means that the percentage of the value, which is obtained by dividing the standard deviation of the length of the short axis and the long axis by the length of the short axis and the long axis, respectively, is preferably 100% or less, more preferably 80% or less, further preferably 50% or less. The shape of the silver salt of an organic acid can be determined from a transmission electron microscope image of silver salt of an organic acid dispersion. Another method for determining monodispersion includes a method involving the step of obtaining the standard deviation of a volume-weighted average diameter of the silver salt of an organic acid. The percentage (coefficient, of variation) of the value obtained by dividing the standard deviation by the volume-weighted average diameter is preferably 100% or less, more preferably 80% or less, further preferably 50% or less. For example, the value can be obtained from a grain size (volume-weighted average diameter) determined by irradiating silver salt of an organic acid dispersed in a solution with a laser ray and determining an autocorrelation function of the scattered light on the basis of the change in time.

The organic acid silver salt used for the present invention can be prepared by reacting (1) a solution containing silver ions in water or in a mixture of an organic solvent and water, and (2) a solution or suspension containing an alkali metal salt of an organic acid in water, in a mixture of an organic solvent and water, or in an organic solvent. Examples of the alkali metal salt of an organic acid include Na salts, K salts, Li salts and so forth. As the solution containing silver ions, a silver nitrate solution can be used. The organic acid alkali metal salt can be obtained by treating the organic acid with an alkali. The preparation of the organic acid silver salt may be performed batchwise or continuously in an appropriate reaction vessel. Stirring in the reaction vessel may be effected by any stirring method depending on required properties of the grains. Any of methods may be used as preparations of the organic acid silver salt, which include a method of gradually or rapidly adding a solution containing silver ions to a reaction vessel containing an organic acid alkali metal solution or suspension, a method of gradually or rapidly adding a organic acid alkali metal salt solution or suspension prepared beforehand to a reaction vessel containing a solution containing silver ions, or a method of simultaneously adding to a reaction vessel a solution containing silver ions and an organic acid alkali metal salt solution or suspension both of which are prepared beforehand.

As the solution containing silver ions and the solution or suspension containing an organic acid alkali metal salt, those having arbitrary concentrations may be used to control the grain size of the organic acid silver salt to be prepared, and may be added at any addition rate. As methods for addition of the solution containing silver ions and the organic acid alkali metal salt solution or suspension, addition at a constant rate or addition at an increasing or decreasing rate according to an arbitrary time function may be applied. The solution may be added to the liquid surface of or into a solution of the reaction system. When a solution containing silver ions and an organic acid alkali metal salt solution or suspension, both are prepared beforehand, are simultaneously added to a reaction vessel, either of the solution containing silver ions and the organic acid alkali metal salt solution or suspension may be added in advance, and in this procedure, the solution containing silver ions is preferably added in advance. The amount added in advance is preferably from 0 to 50% by volume, more preferably from 0 to 25% by volume, of the entire amount to be added. Furthermore, a method described in JP-A-9-127643 wherein pH or silver potential of the reaction solution is controlled during the reaction may be preferably used.

The pH of the solution containing silver ions and the solution or suspension containing an organic acid alkali metal salt to be added may be adjusted depending on the required properties of the grains. For adjusting the pH, any acid or alkali may be added. Furthermore, depending on the required property of the grains, for example, the temperature in the reaction vessel may be suitably chosen to control the grain size of the organic acid silver salt to be prepared. The solution containing silver ions and the organic acid alkali metal salt solution or suspension to be added may also be suitably prepared at any temperature. In order to keep liquid flowability of the solution or suspension of an organic acid alkali metal salt, the solution or suspension is preferably heated and maintained at a temperature of 50° C. or higher.

The organic acid silver salt for use in the present invention is preferably prepared in the presence of a tertiary alcohol. The tertiary alcohol having a total carbon number of 15 or less is preferred, and those having that of 10 or less is most preferred. Examples of preferred tertiary alcohols include tert-butanol. The tertiary alcohol may be added in any timing during the preparation of the organic acid silver salt. The tertiary alcohol is preferably added at the time of preparation of the organic acid alkali metal salt to dissolve the organic alkali metal salt. The tertiary alcohol may be added in any amount of from 0.01 to 10 as weight ratio based on the weight of $H_2O$ used as a solvent for the preparation of the organic acid silver salt, and preferably added in an amount of from 0.03 to 1. Hereafter, the preparation method of the organic acid silver salt will be explained by referring to the use of tertiary alcohol. However, the scope of the present invention is not limited to the methods using a tertiary alcohol.

As the silver ion source, a wafer-soluble silver salt can be used, and silver nitrate is preferred as the water-soluble silver salt. The concentration of silver ion in the solution is preferably 0.03 mole/liter to 6.5 moles/liter, more preferably 0.1 mole/liter to 5 moles/liter. The pH of the aqueous solution is preferably 2 to 6, more preferably 3.5 to 6.

The solution containing silver ions may contain a tertiary alcohol having from 4 to 6 carbon atoms. In that case, the amount of such tertiary alcohol is 70% by volume or less, preferably 50% by volume or less, based on the total volume of the solution containing silver ions. The temperature of the solution is preferably 0° C. to 50° C., more preferably 5° C. to 30° C. In a case where the solution containing silver ions and the aqueous tertiary alcohol solution of an alkali metal salt of an organic acid are simultaneously added in the manner as mentioned below, the temperature is most preferably 5° C. to 15° C.

Specific examples of the alkali metal of the alkali metal salt of an organic acid include sodium salts and potassium salts. The alkali metal salt of an organic acid may be prepared by adding sodium hydroxide or potassium hydroxide to an organic acid. In this step, the amount of the alkali is preferably not larger than the equivalent amount of the organic acid so as to reserve non-reacted organic acid. In this case, the amount of the remaining non-reacted organic acid may be 3 mole % to 50 mole %, preferably 3 mole % to 30 mole %, per mole of the total organic acid. Preparation may also be carried out by adding an alkali in an amount larger than a given amount, and then neutralizing the excess alkali by addition of an acid such as nitric acid or sulfuric acid.

Depending on the required properties of the silver salt of an organic acid, the pH of the reaction system may be controlled. For controlling the pH, any acid or alkali may be used.

The solution containing silver ions, the aqueous tertiary alcohol solution of an alkali metal salt of an organic acid, or the liquid in the reaction vessel may be optionally added with compounds of the formula (1) described in JP-A-62-65035, water-soluble group-containing N-heterocyclic compounds such as those described in JP-A-62-150240, inorganic peroxides such as those described in JP-A-50-101019, sulfur compounds such as those described in JP-A-51-78319, disulfide compounds such as those described in JP-A-57-643, hydrogen peroxide and so forth.

The aqueous tertiary alcohol solution of an alkali metal salt of an organic acid is preferably in a mixed solvent of water and a tertiary alcohol having 4 to 6 carbon atoms to obtain uniformity of the solution. Alcohols in which the number of carbon atoms exceeds the defined range may not be preferred as their miscibility with water becomes poor. Among the tertiary alcohol having 4 to 6 carbon atoms, most preferred is tert-butanol as its water-miscibility is the highest. Alcohols other than tertiary alcohols may be also unfavorable as mentioned above since they have a reducing property and adversely affect the process of forming the silver salt of an organic acid. The amount of the tertiary alcohol that may be used in the aqueous tertiary alcohol solution of an alkali metal salt of an organic acid may be 3% by volume to 70% by volume of a solvent, preferably 5% by volume to 50% by volume, relative to the volume of water in the aqueous solution.

The concentration of the alkali metal salts of an organic acid in the aqueous tertiary alcohol solution of the alkali metal salts of an organic acid may be 7% by weight to 50% by weight, preferably 7% by weight to 45% by weight, more preferably 10% by weight to 40% by weight.

The temperature of the aqueous tertiary alcohol solution of an alkali metal salt of an organic acid to be added in a reaction vessel is preferably from 50° C. to 90° C., more preferably from 60° C. to 85° C., most preferably from 65° C. to 85° C. to keep a temperature sufficient for preventing crystallization or solidification of an alkali metal salt of an organic acid. In order to control a constant reaction temperature, the temperature is preferably controlled at a constant temperature chosen from the above range.

The silver salt of an organic acid preferably used for the present invention may be prepared by i) a method comprising the step of adding an aqueous tertiary alcohol solution of an alkali metal salt of an organic acid as a single portion to a total amount of a solution containing silver ions already put into a reaction vessel, or ii) a method comprising a time period of simultaneous addition of both of a solution containing silver ions and an aqueous tertiary alcohol solution of an alkali metal salt of an organic acid into a reaction vessel (simultaneous addition method). In the present invention, the latter simultaneous addition method is preferred to control mean grain size of the silver salt of an organic acid and to achieve narrow grain size distribution. In this method, it is desirable that at least 30% by volume, more preferably from 50 to 75% by volume, of a total volume to be added is simultaneously added in a reaction vessel. In a case where either one is added in a reaction vessel in advance, it is desirable that the solution containing silver ions is first added in the vessel.

In any case, the temperature of a liquid in a reaction vessel (the liquid means the solution containing silver ions put in a reaction vessel in advance as mentioned above; or when the solution containing: silver ions is not added in a reaction vessel in advance, the liquid means a solvent already put in the vessel in advance as described below) is preferably 5° C. to 75° C., more preferably 5° C. to 60° C., most preferably 10° C. to 50° C. Throughout the reaction process, the reaction temperature is preferably controlled at a constant temperature falling within the above-defined range. The reaction temperature may also be preferably controlled according to several temperature patterns within the above-defined range.

The temperature difference between the liquid in a reaction vessel and the aqueous tertiary alcohol solution of an alkali metal salt of an organic acid is preferably 20° C. to 85° C., more preferably 30° C. to 80° C. The temperature of the aqueous tertiary alcohol solution of an alkali metal salt of an organic acid may preferably be higher than said liquid.

By performing the process as described above, a rate of precipitation as fine crystals, occurred by rapid cooling in a reaction vessel of the aqueous tertiary alcohol solution of an alkali metal salt of an organic acid that is kept at a high temperature, and a rate of forming a silver salt of an organic acid by reaction with the water-soluble silver salt are both favorably controlled, thereby crystal shape, crystal size and crystal size distribution of the silver salt of an organic acid can be preferably controlled. In addition, the properties of thermally processed materials particularly as photothermographic materials can also be improved.

A preferred scaly silver salt of an organic acid for use in the present invention may preferably be prepared by, for example, reacting a solution containing silver ions with an aqueous solution of an alkali metal salt of an organic acid in an aqueous tertiary alcohol solution in a reaction vessel (the method includes a step of adding the aqueous tertiary alcohol solution containing an alkali metal salt of an organic acid into a liquid filled in a reaction vessel), wherein the temperature difference between the liquid already in the reaction vessel and the aqueous tertiary alcohol solution of an alkali metal salt of an organic acid to be added thereto falls between 20° C. and 85° C., wherein the liquid in the reaction vessel is preferably a solution containing silver ions put into the reaction vessel in advance, or alternatively, the liquid is water or a mixed solvent of water and a tertiary alcohol in a case where the solution containing silver ions is not put into the reaction vessel in advance but is added from the start simultaneously with an aqueous solution of an alkali metal salt of an organic acid in a tertiary alcohol, and when the solution containing silver ions is put into the reaction vessel in advance, water or a mixed solvent of water and a tertiary alcohol may be filled in advance.

By maintaining the temperature difference during the addition of the aqueous tertiary alcohol solution containing an alkali metal salt of an organic acid, the crystal shape of the silver salt of an organic acid or the like can favorably controlled.

The reaction vessel may contain a solvent beforehand, and water is preferably used as the solvent filled in advance. A mixed solvent of water and a tertiary alcohol may also be preferably used.

According to the present invention, a dispersing agent having a molecular weight of 3000 or less is added and dispersed before the reaction of a solution containing silver ions (water or a mixture of water and an organic solvent is used as a solvent) and a solution or dispersion of an alkali metal salt of an organic acid (water, a mixture of water and an organic solvent, or organic solvent is used as a solvent or dispersion medium) or before the desalting operation. Such a surfactant can be added to either of the solution containing silver ions or the solution of an alkali metal salt of an organic acid, or to the both. The surfactant may also be added to a liquid placed in a reaction vessel beforehand, or the surfactant may be added to the reaction system as a solution separately prepared by dissolving it in water, a mixture of water and an organic solvent, or an organic solvent. These addition methods may be arbitrarily combined.

The dispersing agent may be any compound so long as the agent can disperse the formed silver salt of an organic acid and has a molecular weight of 3000 or less. The molecular weight is preferably 100 to 3000, more preferably 100 to 2000. Examples of the dispersing agent include, for example, anionic surfactants such as carboxylic acid salts, sulfuric acid ester salts, sulfonic acid salts, and phosphoric acid ester salts, polyalcohol type nonionic surfactants, polyethylene glycol type nonionic surfactants, cationic surfactants such as primary amine salts, secondary amine salts and tertiary amine salts, oligomers thereof and so forth. Preferably, a dispersing agent having a sulfonic acid group in the molecule is used. Examples of the dispersing agent having a molecular weight of 3000 or less include sodium tetradecane 2,3-ene-1-sulfonate (molecular weight: 299), triisopropylnaphthalenesulfonic acid (molecular weight: 357), naphthalenesulfonic acid oligomer (average molecular weight: 1250) and so forth.

The amount of the dispersing agent having a molecular weight of 3000 or less may vary depending on the grain size, the kind of the dispersing agent to be used and so forth, and the amount is not particularly limited so long that the amount does not cause aggregation of the organic acid silver salt to be obtained. However, the agent is used usually in an amount of 0.1 to 30% by weight, particularly preferably 0.5 to 15% by weight, of the organic acid silver salt.

As for the time point of the addition of the dispersing agent having a molecular weight of 3000 or less, it is particularly preferred to add before completion of the addition of the solution containing silver ions, because the grains become likely cause aggregation when hydrophilic alkali metal salt of an organic acid reacts with. silver ions and changes into hydrophobic organic acid silver salt.

A preferred dispersing agent having a molecular weight of 3000 or less is an anionic surfactant that is soluble in water or a mixture of water and organic solvent for the use in the reaction (the medium may be referred to as "aqueous medium"). The anionic surfactant may be any compound so long as it can disperse the formed organic acid silver salt and has 8 to 40 carbon atoms. The number of carbon atoms is more preferably 12 to 40.

The hydrophilic group may be any group so long as the group is an anionic such as carboxylic acid salts, sulfuric acid ester salts, sulfonic acid salts and phosphoric acid ester salts. However, a sulfuric acid ester salt or sulfonic acid salt is preferred, and at least one aromatic group is preferably contained, from a viewpoint that dispersion stability is imparted in high ionic strength circumstance due to the byproduct salts generated by the reaction of a solution containing silver ions and a solution of alkali metal salt of an organic acid.

The amount of the anionic surfactant may vary depending on the kind of the surfactant to be used and grain size of the organic acid silver salt, and it is not particularly limited so long as the amount is sufficient to obtain stably dispersed organic acid silver salt. However, in order to obtain an adsorption rate that can follow the generation rate of the organic acid silver salt grains, the amount is preferably 5 to 100 times the critical micelle concentration, more preferably 20 to 80 times the critical micelle concentration of surfactant.

In the present invention, a dispersing agent having a molecular weight of more than 3000 can further be used in combination. Such a dispersing agent can suitably be selected for use from synthetic known polymers, for example, synthetic anionic polymers such as polyacrylic acid, naphthalenesulfonic acid polymers, copolymers of acrylic acid, maleic acid copolymers, maleic acid monoester copolymers and copolymers of acryloylmethylpropanesulfonic acid; semi-synthetic anionic polymers such as carboxymethyl starch and carboxymethylcellulose; anionic polymers such as alginic acid and pectic acid; other polymers including polyvinyl alcohol (e.g., PVA-217 (trade name), mean polymerization number: about 1700), polyvinylpyrrolidone, carboxymethylcellulose, hydroxypropylcellulose, hydroxypropylmethylcellulose etc., naturally occurring macromolecular compounds such as gelatin and so forth.

As the dispersing agent having a molecular weight of more than 3000, a nonionic macromolecular dispersing agent can preferably be used. More preferred is a nonionic macromolecular dispersing agent soluble in a reaction aqueous medium, which can disperse a silver salt of an organic acid and has a molecular weight of 5 times to 10 times the fractional molecular weight of an ultrafiltration membrane used for the desalting of the byproduct salt produced from the reaction of the solution containing silver ions and the solution of alkali metal salt of an organic acid. As such a dispersing agent, polyvinyl alcohol; polyvinylpyrrolidone and hydroxypropylcellulose can preferably be used.

The concentration of the dispersing agent having a molecular weight of more than 3000, preferably a nonionic macromolecular dispersing agent, is preferably 0.1 to 30% by weight, particularly preferably 0.5 to 30% by weight, of the silver salt of an organic acid. While the addition time of the dispersing agent having a molecular weight of more than 3000, preferably a nonionic macromolecular dispersing agent, is not particularly limited, the agent is preferably added after completion of the reaction of the silver salt of an organic acid and,before completion of the desalting operation to prevent inhibition of the reaction of the silver salt of an organic acid.

According to a further preferred embodiment, after the desalting operation is performed by ultrafiltration and thus the conductivity of the organic acid silver salt dispersion is reduced, the dispersing agent having a molecular weight of more than 3000, preferably a nonionic macromolecular dispersing agent, can be added. The conductivity at this time point is preferably 2,000 $\mu$S/cm or less.

In this case, it is preferable to conduct an operation of adding pure water in an amount of 2-fold to 10-fold of the amount of the anionic surfactant solution permeated through the ultrafiltration membrane, i.e., so-called constant volume dilution, to remove the dispersing agent having a molecular weight of 3000 or less, preferably an anionic surfactant having a hydrophobic group with 8 to 40 carbon atoms, and replace said surfactant with the dispersing agent having a molecular weight of more than 3000, preferably a nonionic macromolecular dispersing agent.

The desalting method used for the present invention may be any method that can provide the desired desalting effect. Ultrafiltration can be preferably used.

The ultrafiltration can be performed in a manner used for, for example, desalting and concentration of silver halide emulsion, and for example, Research Disclosure, No. 10 208 (1972), No. 13 122; (1975), No. 16 351 (1977) etc. can be referred to. While pressure difference, flow rate etc., which are important as the operational conditions, can be selected by referring to the characteristic curves mentioned in Haruhiko Oya, "Membrane Utilization Technique Handbook", published by Saiwai Shobo (1978), p.275, it is necessary to determine optimum conditions for treating a given organic acid silver salt dispersion to suppress aggregation of grains, fog and so forth. Further, as for a method where a solvent is supplemented for compensating the loss due to the membrane permeation, there are the constant volume method where the solvent is continuously supplemented, and the batch method where the solvent is intermittently added. The constant volume method is preferred because of its relatively shorter desalting treatment time. Pure water obtained by ion exchange or distillation is used as the solvent to be supplemented as described above. In order to maintain pH; concentration of the dispersing agent, concentration of a poor solvent for the dispersing agent at intended levels according to the present invention, a pH modifier; dispersing agent, poor solvent for the dispersing agent etc. may be added to pure water for the solvent to be supplemented or directly added to the organic acid silver salt dispersion.

In particular, because the organic acid silver salt grains are in a state that is likely to aggregate in a high salt concentration circumstance of the early stage of the desalting operation and in a presence of an organic solvent such as tertiary alcohol, the concentration of the ionic surfactant having anionic nature and a hydrophobic group with 8 to 40 carbon atoms is preferably maintained at a level 5 to 100 times as high as the critical micelle concentration of surfactant. Specifically, while the concentration of leaking surfactant is quantified by spectrophotometry or liquid chromatography, a solution having the same concentration as the measured concentration may be continuously added as a replenisher, or a solution having a concentration higher than that may be added intermittently.

Further, since the silver salt of an organic acid is extremely hydrophobic, aggregation may highly proceed under a shearing field or pressure field during the feeding operation and passage through an ultrafiltration membrane. Furthermore, in a high ionic strength circumstance in early stages of the desalting operation, the surface charge of the organic acid silver salt grains is shielded, and hence they become more likely cause aggregation. In order to ameliorate this condition, another ionic surfactant having anionic nature an d a hydrophobic group with 8 to 40 carbon atoms different from the anionic surfactant added beforehand may be added during the desalting operation, and this method constitute a preferred embodiment of the present invention. As for the addition method, while the concentration of leaking surfactant is quantified by spectrophotometry or liquid chromatography, a solution having the same concentration as the measured concentration may be continuously added, or a solution having a concentration higher than that may be added intermittently, as described above.

As an ultrafiltration membrane, modules of plate type, spiral type, cylinder type, hollow yarn type, hollow fiber type and so forth, in which a membrane is already incorporated, are commercially available from Asahi Chemical Industry Co., Ltd., Daicel Chemical Industries, Ltd., Toray Industries, Inc., NITTO DENKO CORP. and so forth. From viewpoints of total membrane area, washability and so forth, those of spiral type and hollow yarn type are preferred. The fractional molecular weight, which is an index of a threshold of substances that can permeate a membrane, should be determined based on the molecular weight of the used dispersing agent, preferably an ionic surfactant having anionic nature and a hydrophobic group with 8 to 40 carbon atoms. Since the molecular weight of the anionic surfactant typically used in the present invention is 150 to 1,000, those having a molecular weight 10 times as much as that molecular weight, i.e., 1,500 to 50,000, or more are used.

If the fractional molecular weight of an ultrafiltration membrane is unknown, its ratio of rejection can be obtained by filtering a solution of a dispersing agent to be used, preferably an anionic surfactant, and calculating the ratio from the concentration of the surfactant leaked into the filtrate. When an anionic surfactant is used, the ratio of rejection "R" of an ultrafiltration membrane is defined by the following equation:

$$R=(Ci-Co)/Ci \times 100[\%]$$

wherein Ci represent a concentration of original solution, and Co represents a permeated concentration in the filtrate.

The ratio of rejection is preferably less than 50% for the method of the present invention.

Since a silver salt of an organic acid not containing a dispersing agent beforehand is extremely hydrophobic, not only crosslinking between grains proceeds with time, but also aggregation markedly progresses under a shearing field or pressure field during the feeding operation and passage through an ultrafiltration membrane. Furthermore, under a high ionic strength circumstance before the desalting operation, the surface charge of the organic acid silver salt grains is shielded, and hence they become more likely cause aggregation. In order to ameliorate this condition, it is desirable that high pH condition is maintained so that dissociation of species present on -grain surfaces should be accelerated. However, if the alkalinity in the circumstance becomes too high, actions of silver oxide or impurity reducing substances may be enhanced to cause fog. Therefore, according to the present invention, it is preferable to maintain pH of the dispersion to be 6 or higher, more preferably 6 to 9, until the conductivity is made to be below $1000 \mu S/cm$ by the desalting operation, so that stable ultrafiltration operation can be performed without aggregation even under a high ionic strength circumstance.

The liquid temperature is preferably kept low until the desalting progresses after the formation of grains. This is because, in a state that the organic solvent used for dissolving the alkali metal salt of an organic permeates the produced organic acid silver salt grains, silver nuclei are likely to be formed by the shearing field and the pressure field during the feeding of the liquid or the passage through the ultrafiltration membrane. Therefore, according to the present invention, the ultrafiltration is performed while the temperature of the organic acid silver salt dispersion is maintained at 1 to 30° C., preferably 5 to 25° C.

In the present invention, it is also possible to carry out the ultrafiltration operation while adding a poor solvent for the dispersing agent used after the conductivity reaches below $1,000 \mu S/cm$ with the progress of the desalting. Under a low ionic strength circumstance, aggregation is not caused even if the protection effect of the dispersing agent is reduced, because stabilizing effect is exerted by electric charge on the grain surfaces. In addition, the viscosity of the whole dispersion becomes high due to increase of repulsion between the grains, and therefore the filtration operation becomes difficult. In order to avoid this phenomenon, it is desirable to add the poor solvent for the dispersing agent.

The produced dispersion can be stored with stirring to prevent precipitation of the grains during storage, or stored in a highly viscous state formed with hydrophilic colloids (e.g., a jelly state formed with gelatin). Further, it may be added with a preservative to prevent saprophytic proliferation during the storage.

The organic acid silver salt dispersion of the present invention contains at least a silver salt of an organic acid and water. The ratio of the silver salt of an organic acid and water is not particularly limited, and the ratio can be suitably selected to efficiently form a coated layer in view of rheological characteristics for stable coating, production speed determined by dry moisture content and so forth. The ratio of the silver salt of an organic acid based on the whole dispersion is preferably 10 to 50% by weight, particularly preferably 10 to 30% by weight. In the method of the present invention, after the conductivity reaches to 20 $\mu S/cm$ or more to less than 300 $\mu S/cm$ due to the desalting operation by the ultrafiltration, the dispersion can be concentrated to a concentration of 10 to 70% by weight, preferably 10 to 50% by weight, particularly preferably 10 to 30% by weight.

In the present invention, metal ions selected from Ca, Mg, Ce, Al, Zn and Ba are preferably added in the form of a water-soluble metal salt, which is not a halide compound. Specifically, they are preferably added in the form of nitrate or sulfate.

Time to add the metal ions selected from Ca, Mg, Ce, Al, Zn and Ba is not particularly limited, and they may be, added any time. For example, they may be added to a liquid of organic acid silver salt preparation, added beforehand to a reaction mixture, added during or immediately after the formation of the organic acid silver salt, or immediately before the coating, i.e., before or after the formation of coating solution. The amount is preferably $10^{-3}$ to $10^{-1}$ mole, particularly preferably $5 \times 10^{-3}$ to $5 \times 10^{-2}$ mole, per one mole of the organic acid silver salt.

As for the method and condition for mixing the separately prepared photosensitive silver halide and silver salt of an organic acid, for example, a method wherein silver halide grains and silver salt of an organic acid after completion of their preparation may be mixed by a high-speed mixer, ball mill sand mill, colloid mill, vibration mill, homogenizer or the like, or a method wherein a silver salt of an organic acid may be produced by mixing a photosensitive silver halide after completion of its preparation at any time during the preparation of the silver salt of an organic acid may be applied. However, they are not particularly limited so long as the advantages of the present invention can be obtained. It is desirable to finely disperse prepared silver salt of an organic acid in water and add silver halide into the dispersion as described below.

The organic acid silver salt dispersion may be subjected to mechanical dispersion process using a dispersing machine so far that the photographic performances are not degraded. A dispersing method, a method is preferred which comprises steps of preparing an aqueous dispersion of the silver salt of an organic acid, forming a high-pressure and high-speed flow of the aqueous dispersion, and re-dispersing the salt by lowering the pressure to form a fine aqueous dispersion of the salt. In this process, the dispersion medium preferably consists of water alone, but may contain an organic solvent at an amount of 20% by weight or less.

The dispersing apparatuses and techniques used for performing the above-described re-dispersion method are described in detail, for example, in Toshio Kajiuchi and Hiromoto Usui, Bunsan-kei Rheology to Bunsanka Gijutsu (Rheology of Dispersion System and Dispersion Technology), pp.357–403, Shinzan Sha Shuppan (1991), and Kagaku Kogaku no Shinpo (Progress of Chemical Engineering), vol. 24, pp. 184–185, compiled by Corporation Kagaku Kogakukai Tokai Shibu, Maki Shoten (1990), JP-A-59-49832, U.S. Pat. No. 4,533,254, JP-A-8-137044, JP-A-8-238848, JP-A-2-261525, JP-A-1-94933 and so forth. The re-dispersion method used in the present invention comprises the steps of supplying a water dispersion containing at least a silver salt of an organic acid into a pipeline under a positive pressure by means of a high-pressure pump or the like, passing the dispersion through a narrow slit provided inside the pipeline, and then subjecting the dispersion to rapid pressure release to perform fine dispersion.

As for the high-pressure homogenizer, it is generally considered that uniform dispersion can be efficiently achieved by increasing (a) "shear force" generated during the passage of a dispersoid through a narrow slit (approximately from 75 $\mu$m to 350 $\mu$m) under high pressure at a high speed and (b) "cavitation force" generated by the pressure releasing without changing the preceding impact force resulting from liquid-liquid collision or liquid-wall collision in the high-pressured narrow space. One old example of the dispersion apparatus of this type is a Golline homogenizer. In this apparatus, a liquid to be dispersed which is introduced under high pressure is converted into a high-speed flow in a narrow gap formed on the wall of a cylindrical surface. Then, the flow collides against a surrounding wall with its own energy, and is emulsified and dispersed by the impact force. Examples of apparatuses for the liquid-liquid collision mentioned above include, for example, a Y-type chamber of a microfluidizer, a spherical chamber utilizing a spherical check valve such as that described in JP-A-8-103642 mentioned below and the like. An example of an apparatus for the liquid-wall collision includes a Z-type chamber of microfluidizer and the like. The pressure applied is generally from 100 to 600 kg/cm$^2$, and the flow rate is generally a few meters/sec to 30 meters/sec. In order to increase dispersion efficiency, some apparatuses are designed wherein a high flow rate area is modified to have a serrated configuration, thereby the frequency of collision is increased. Typical examples of such devices are Golline homogenizer, Microfluidizer from Microfluidex International Corporation, Microfluidizer from Mizuho Kogyo Co., Ltd., Nanomizer from Tokushu Kika Kogyo Co., Ltd and the like. Other examples of such apparatuses are described in JP-A-8-238848, JP-A-8-103642 and U.S. Pat. No. 4,533,254.

The silver salt of an organic acid can be dispersed to have a desired grain size by controlling a flow rate, a differences in pressure achieved by pressure releasing and the frequency of processing. From viewpoints of photographic performances and the grain size, the flow rate is preferably from 200 to 600 m/sec and the difference in pressure at pressure releasing is preferably from 900 to 3,000 kg/cm$^2$, and more preferably, the flow rate is from 300 to 600 m/sec, and the difference in pressure at pressure releasing is from 1,500 to 3,000 kg/cm$^2$. The frequency of the dispersion processing may be appropriately chosen as required, and frequency of 1 to 10 times may generally be chosen. From a viewpoint of productivity, the frequency of approximately from 1 to 3 times is chosen. Warming of a water dispersion at a high temperature under a high pressure is not desired from viewpoints of dispersibility and photographic performance. At a high temperature above 90° C., a grain size may readily become large and fog may be increased. Accordingly, a cooling apparatus may preferably be provided in a step before the conversion into a high-pressure and high-speed flow, or a step after the pressure release, or both of the steps, and a temperature of the water dispersion is preferably kept by the cooling step at from 5° C. to 90° C., more preferably from 5° C. to 80° C., most preferably from 5° C. to 65° C. It is particularly effective to provide the cooling step when dispersing is carried out under a high pressure of from 1,500 to 3,000 kg/cm$^2$. The cooling apparatus may be appropriately selected from a double pipe or triple pipe provided with a static mixer, a multi-tubular exchanger, a coiled heat exchanger and the like depending on an amount of heat exchange to be required. The size, wall thickness or material of a pipe may be appropriately selected to increase heat exchange efficiency depending on an applied pressure. In addition, depending on an amount of heat exchange, a refrigerant used in the cooling apparatus may be a well water at 20° C. or a chilled water at from 5 to 10° C. cooled by a refrigerator, and if desired, a refrigerant such as ethylene glycol/water at −30° C. may also be used.

When a photosensitive silver halide salt coexists at the time of dispersing process of the silver salt of an organic acid, fog may increase and sensitivity may markedly decrease. Therefore, the dispersion during the dispersing process preferably contains substantially no photosensitive silver halide salt. The amount of photosensitive silver halide salt in the; aqueous dispersion to be dispersed is desirably 0.1 mole % or less per 1 mole of silver salt of an organic acid in the dispersion, and it is desirable not to intentionally add photosensitive silver halide salt.

Other than the mechanical dispersion, the silver salt of an organic salt can be made into grains by roughly dispersing the salt in a solvent through pH control, and then changing the pH in the presence, of a dispersing aid. For the operation, an organic solvent may be used as a solvent for the rough dispersion, and such organic solvent is usually removed after the formation of grains.

The silver salt of an organic acid prepared by a method for preparing silver salts of an organic acid is preferably finely dispersed in an aqueous solvent, and then mixed with an aqueous solution of a photosensitive silver halide salt to provide a coating solution for photosensitive image-forming layer. Use of such a coating solution enables the manufacture of a photothermographic material exhibiting low haze and low fog, and having high sensitivity. When a photosensitive silver halide salt coexists at the time of finely dispersing the silver salt of an organic acid by converting the dispersion into a high-speed flow under a high pressure, fog may increase.and sensitivity may markedly decrease. Therefore, the aqueous dispersion that is dispersed while it is converted into a high-speed flow under high pressure preferably contains substantially no photosensitive silver halide salt. Furthermore, when an organic solvent is used as a dispersion medium instead of water, haze and fog may increase and sensitivity may likely be decreased. On the other hand, when a conversion method where a part of the silver salt of an organic acid in the dispersion is converted into a photosensitive silver halide salt is used instead of the method of mixing an aqueous photosensitive silver halide salt solution, sensitivity may be decreased.

The grain size (volume-weighted average diameter) in the solid fine grain dispersion of silver salt of an organic acid can be determined from a grain size (volume-weighted average diameter) determined by irradiating the solid fine grain dispersion dispersed in a liquid with a laser ray and determining an autocorrelation function of the scattered light on the basis of the change in time. The solid fine grain dispersion having an average grain size of from 0.05 to 10.0 $\mu$m is preferred. An average grain size of from 0.1 to 5.0 $\mu$m may be more preferred, and from 0.1 to 2.0 $\mu$m may be further preferred.

The mixing ratio of the silver salt of an organic acid and the photosensitive silver halide salt may be chosen depending on a purpose. The ratio of the photosensitive silver halide salt to the silver salt of an organic acid is preferably from 1 to 30 mole %, more preferably from 3 to 20 mole %, most preferably from 5 to 15 mole %. Two or more different aqueous dispersions of silver salt of an organic acid are preferably mixed with two or more different photosensitive silver halide salt aqueous dispersions, which method may be preferably applied to control photographic properties.

The silver salt of an organic acid may be used in any desired amount in the photothermographic material. The amount is preferably from 0.1 to 5 g/m$^2$, more preferably from 1 to 3 g/m$^2$ as the weight of silver.

The photothermographic material of the invention contains a reducing agent for silver salt of an organic acid. The reducing agent for silver salt of an organic acid may be any substance capable of reducing silver ions into silver, preferably an organic substance. Some examples of the reducing agent are described in JP-A-11-65021, paragraphs 0043 to 0045 and EP 0803764A1, from page 7, line 34 to page 18, line 12. For the use in the present invention, bisphenol-type reducing agents (e.g., 1,1-bis(2-hydroxy-3,5-dimethylphenyl)-3,5,5-trimethylhexane) are particularly preferred. The amount of the reducing agent is preferably from 0.01 to 5.0 g/m$^2$, more preferably from 0.1 to 3.0 g/m$^2$. The amount of the reducing agent is preferably 5 to 50 mole %, more preferably 10 to 40 mole %, per mole of silver on the side of the image-forming layer.

The reducing agent may be contained in a coating solution in any state, for example, in a state of solution, emulsified dispersion, solid microparticle dispersion or the like. It may be contained in any layer of the photosensitive material of the present invention.

As a well known emulsification method, there can be mentioned a method of mechanically preparing an emulsified dispersion by using an oil such as dibutyl phthalate, tricresyl phosphate, glyceryl triacetate or diethyl phthalate, ethyl acetate or cyclohexanone as an auxiliary solvent for dissolution.

As a solid microparticle dispersion method, examples include a method of preparing a solid dispersion by dispersing powder of the reducing agent in a suitable solvent such as water using a ball mill, colloid mill, vibrating ball mill, sand mill, jet mill, roller mill or the like or by means of ultrasonic wave. In this operation, a protective colloid (e.g., polyvinyl alcohol), a surfactant (e.g., an anionic surfactant such as sodium triisopropylnaphthalenesulfonate (mixture of those having three isopropyl groups on different positions)) and so forth may be used. An aqueous dispersion may contain a preservative (e.g., benzisothiazolinone sodium salt).

The photosensitive silver halide which can be used for the present invention is not particularly limited as for halogen composition, and silver chloride, silver chlorobromide, silver bromide, silver iodobromide, and silver chloroiodobromide may be used. Distribution of the halogen composition may be uniform in the grains, or alternatively, the halogen composition may alter stepwise or continuously in the grains. Silver halide grains having a core/shell structure may preferably be used. A double to quintuple structure is preferred, and more preferably, core/shell grains having a double to quadruple structure may be used. A technique for localizing silver bromide on the surface of silver chloride or silver chlorobromide grains may also be preferably used.

Preparations of the photosensitive silver halide are well known in the art. For example, methods described in Research Disclosure, No. 17029 (June, 1978) and U.S. Pat. No. 3,700,458 can be used. More specifically, a method can be used which comprises the step of preparing photosensitive silver halide grains by addition of a silver-supplying compound and a halogen-supplying compound to a solution of gelatin or other polymer, and then adding a silver salt of an organic acid to the resulting grains.

The grain size of the photosensitive silver halide is preferably made small in order to suppress turbidity after image formation. Specifically, the grain size may preferably be 0.20 μm or less, more preferably from 0.01 to 0.15 μm, further preferably from 0.02 to 0.12 μm. The term "grain size" used herein means a diameter of a sphere having the same volume as the grain where the silver halide grains are regular crystals in cubic or octahedral form and where the silver halide grains are irregular crystals such as spherical or rod-like grains. Where silver halide grains are tabular grains, the term means the diameter of a circle having the same area as a projected area of the main surface of the tabular grain.

Examples of the form of silver halide grains include a cubic form, octahedral form, tabular form, spherical form, rod-like form and potato-like form. In particular, cubic grains are preferred for the present invention. Silver halide grains having round corners are also preferably used in the present invention. Surface index (Miller index) of outer surfaces of the photosensitive silver halide grains is not particularly limited. It is desired that [100] face be present in a high proportion that can achieve high spectral sensitizing efficiency when a spectral sensitizing dye adsorbs thereto. The proportion of [100] face may be preferably not lower than 50%, more preferably at least 65%, still more preferably at least 80%. The proportion of Miller index [100] face can be determined using the method described in T. Tani, J. Imaging Sci., 29, 165 (1985), where the difference in adsorption property of a sensitizing dye to [111] face and [100] face is utilized.

The photosensitive silver halide grain of the present invention desirably contains a metal or metal complex of Group VIII to Group X in the periodic table of elements (including Group I to Group XVIII). The metal or the center metal of the metal complex of Group VIII to X of the periodic table is preferably rhodium, rhenium, ruthenium, osmium or iridium. The metal complex may be used alone, or two or more complexes of the same or different metals may also be used in combination. The metal complex content is preferably from $1 \times 10^{-9}$ to $1 \times 10^{-3}$ mole per mole of silver. Such metal complexes are described in JP-A-11-65021, paragraphs 0018 to 0024.

Among them, an iridium compound is preferably contained in the silver halide grains. Examples of the iridium compound include hexachloroiridium, hexammineiridium, trioxalatoiridium, hexacyanoiridium and pentachloronitrosyliridium. The iridium compound is used after dissolving the compound in water or an appropriate solvent, and a method commonly used for stabilizing the iridium compound solution, more specifically, a method comprising adding an aqueous solution of hydrogen halogenide (e.g., hydrochloric acid, hydrobromic acid, hydrofluoric acid) or halogenated alkali (e.g., KCl, NaCl, KBr, NaBr) may be used. Instead of using water-soluble iridium, different silver halide grains doped beforehand with iridium may be added and dissolved at the time of preparation of silver halide. The amount of the iridium compound is preferably $1 \times 10^{-8}$ to $1 \times 10^{-3}$ mole, more preferably 1 $10^{-7}$ to 5 $10^{-4}$ per mole of silver halide.

Metal complexes that can be contained in the silver halide grains used for the present invention (e.g., $[Fe(CN)_6]^{4-}$), desalting methods and chemical sensitization methods are described in JP-A-11-84574, paragraphs 0046 to 0050 and JP-A-11-65021, paragraphs 0025 to 0031.

In the photothermographic material of the present invention, one kind of photosensitive silver halide emulsion may be used or two or more different emulsions (for example, those having different average grain sizes, different halogen compositions, different crystal habits or different chemical sensitization conditions) may be used in combination. By using plural photosensitive silver halides having different sensitivities, contrast can be controlled. Examples of the techniques in the art includes those mentioned in JP-A-57-119341, JP-A-53-106125, JP-A-47-3929, JP-A-48-55730, JP-A-46-5187, JP-A-50-73627, JP-A-57-150841 and so forth. Each emulsion may preferably have sensitivity difference of 0.2 log E or higher.

The amount of the photosensitive silver halide is preferably 0.03 to 0.6 g/m$^2$, more preferably 0.05 to 0.4 g/m$^2$, most preferably 0.1 to 0.4 g/m$^2$, as the amount of coated silver per 1 m$^2$ of a photosensitive material. The amount of the photosensitive silver halide per mole of the silver salt of an organic acid is preferably from 0.01 to 0.5 mole, more preferably from 0.02 to 0.3 mole, still more preferably from 0.03 to 0.25 mole.

Preferred time for addition of a photosensitive silver halide to a coating solution for image-forming layer resides in a period of from 180 minutes before coating to just before coating, preferably 60 minutes to 10 seconds before coating. Methods and conditions for mixing are not particularly limited so long as the effect of the present invention can be obtained satisfactorily. Specific examples of the mixing method include a method in which a mixing is performed in a tank designed so as to obtain a desired average residence time which is calculated from addition flow rate and feeding amount to a coater, a method utilizing a static mixer described in N. Harnby, M. F. Edwards, A. W. Nienow, "Ekitai Kongo Gijutsu (Techniques for Mixing Liquids)", translated by Koji Takahashi, Chapter 8, Nikkan Kogyo Shinbunsha, 1989 and so forth.

An effective binder to be contained in the image-forming layer is one that is soluble or dispersible in an aqueous medium (water or a mixture of water and organic solvent), in particular, one contained as a polymer latex having an equilibrium moisture content of 2 weight % or less at 25° C. and relative humidity of 60%. In the most preferred embodiment, the polymer latex is prepared to have an ion conductivity of 2.5 mS/cm or less. An example of a method for preparing such polymer latex includes a method comprising the step of synthesizing a polymer and then purifying the polymer by using a functional membrane for separation.

The aqueous solvent in which the polymer binder is soluble or dispersible is water or water mixed with 30% by weight or more of a water-miscible organic solvent. Examples of the water-miscible organic solvent include, for example, alcohols such as methyl alcohol, ethyl alcohol and propyl alcohol; cellosolves such as methyl cellosolve, ethyl cellosolve and butyl cellosolve; ethyl acetate, dimethylformamide and so forth. The term "aqueous solvent" used herein also encompasses systems in which a polymer is not thermodynamically dissolved but is present in a so-called dispersed state.

The definition "equilibrium moisture content at 25° C. and relative humidity of 60%" used herein can be represented by the following equation, in which W1 indicates the weight of a polymer at humidity-conditioned equilibrium at 25° C. and relative humidity of 60%, and W0 indicates the absolute dry weight of the polymer at 25° C.

Equilibrated moisture content at 25° C. and relative humidity of 60%

$$=[(W1-W0)/W0]\times 1090 \text{ (weight \%)}$$

As for details of the definition of moisture content and methods for measurement, for example, Lecture of Polymer Engineering, 14, Test Methods for Polymer Materials (Polymer Society of Japan, Chijin Shokan) can be referred to.

The equilibrium moisture content at 25° C. and relative humidity of 60% of the binder polymer is preferably 2% by weight or less, more preferably from 0.01 to 1.5% by weight, most preferably from 0.02 to 1% by weight. In the present invention, polymers dispersible in aqueous solvents are particularly preferred. Examples of systems in the dispersed state include, for example, polymer latex in which fine solid particles of polymer are dispersed, and a system in which a polymer is dispersed in a molecular state or as micelles, both of which are preferred.

In preferred embodiments of the invention, hydrophobic polymers such as acrylic resins, polyester resins, rubber resins (e.g., SBR resins), polyurethane resins, polyvinyl chloride resins, polyvinyl acetate resins, polyvinylidene chloride resins, and polyolefin resins can preferably be used. The polymers may be linear, branched or crosslinked. They may be so-called homopolymers in which a single kind of monomer is polymerized, or copolymers in which two or more different kinds of monomers are polymerized. The copolymers may be random copolymers or block copolymers. The polymers may have a number average, molecular weight of 5,000 to 1,000,000, preferably from 10,000 to 200,000. Polymers having a too small molecular weight fail to give sufficient mechanical strength of an emulsion layer, and those having a too large molecular weight yield bad film forming property, and both of which are not preferred.

The "aqueous solvent" mentioned above means a dispersion medium of which composition comprises at least 30% by weight of water. As for a state of dispersion, systems in any state may be used, for example, emulsion dispersion, micellar dispersion, molecular dispersion of a polymer having a hydrophilic moiety in the molecule and so forth. Among them, polymer latex is particularly preferred.

Preferred examples of the polymer latex are shown below. They are described as monomers as starting materials. The numerals parenthesized are indicated as % by weight, and the molecular weights are number average molecular weights.

P-1: Latex of -MMA(70)-EA(27)-MAA(3)- (molecular weight: 37000)
P-2: Latex of -MMA(70)-2EHA(20)-St(5)-AA(5)- (molecular weight: 40000)
P-3: Latex of -St(50)-Bu(47)-MMA(3)- (molecular weight: 45000)
P-4: Latex of -St(68)-Bu(29)-AA(3)- (molecular weight: 60000)
P-5: Latex of -St(70)-Bu(27)-IA(3)- (molecular weight: 120000)
P-6: Latex of -St(75)-Bu(24)-AA(1)- (molecular weight: 108000)
P-7: Latex of -St(60)-Bu(35)-DVB(3)-MAA(2)- (molecular weight: 150000)
P-8: Latex of -St(70)-Bu(25)-DVB(2)-AA(3)- (molecular weight: 280000)
P-9: Latex of -VC(50)-MMA(20)-EA(20)-AN(5)-AA(5)- (molecular weight: 80000)
P-10: Latex of -VDC(85)-MMA(5)-EA(5)-MAA(5)- (molecular weight: 67000)

P-11: Latex of -Et(90)-MAA(10)- (molecular weight: 12000)

P-12: Latex of -St(70)-2EHA(27)-AA(3)- (molecular weight: 130000)

P-13: Latex of -MMA(63)-EA(35)-AA(2)- (molecular weight: 33000)

Abbreviations in the above formula represents the following monomers:

MMA: methyl methacrylate
EA: ethyl acrylate
MAA: methacrylic acid
2EHA: 2-ethylhexyl acrylate
St: styrene
Bu: butadiene
AA: acrylic acid
DVB: divinylbenzene
VC: vinyl chloride
AN: acrylonitrile
VDC: vinylidene chloride
Et: ethylene
IA: itaconic acid The polymer latexes mentioned above are commercially available, and those mentioned below can be used. Examples of acrylic resins include CEBIAN A-4635, 46583, 4601 (all from Daicel Chemical Industries), Nipol Lx811, 814, 821, 820, 857 (all from Nippon Zeon) and so forth; examples of polyester resins include FINETEX ES650, 611, 675, 850 (all from Dai-Nippon Ink and Chemicals), WD-size, WMS (both from Eastman Chemical) and so forth; examples of polyurethane resins include HYDRAN AP10, 20, 30, 40 (all from Dai-Nippon Ink and Chemicals) and so forth; examples of rubber resins are LACSTAR 7310K, 3307B, 4700H, 7132C (all from Dai-Nippon Ink & Chemicals), Nipol Lx416, 410, 438C, 2507 (all from Nippon Zeon) and so forth; examples of polyvinyl chloride resins include G351, G576 (both from Nippon Zeon) and so forth; examples of polyvinylidene chloride resins are L502, L513 (both from Asahi Chemical Industry) and so forth; examples of polyolefin resins include CHEMIPEARL S120, SA100 (both from Mitsui Petrochemical) and so forth. These polymer latexes may be used alone, or two or more of them may be blended as required.

As the polymer latex used for the production of the photothermographic material of the present invention, styrene/butadiene copolymer latex is particularly preferred. In the styrene/butadiene copolymer, the weight ratio of styrene monomer units to butadiene monomer units is preferably 40/60 to 95/5. The ratio of the styrene monomer units and the butadiene monomer units in the copolymer may preferably be from 60 to 99% by weight. The preferred range of the molecular weight of the copolymer is similar to that mentioned above.

Examples of styrene/butadiene copolymer latexes preferably used for the present invention include the aforementioned P-3 to P-8, commercially available products, LACSTAR-3307B, 7132C, Nipol Lx416 and so forth.

The image-forming layer of the photothermographic material of the present invention may preferably be those formed by using polymer latex. The amount of the binder in the layer containing a silver salt of an organic acid may be 1/10 to 10/1, more preferably 1/5 to 4/1 as indicated by a weight ratio of a total binder/a silver salt of an organic acid.

The image-forming layer of the photothermographic material of the present invention may optionally be added with a hydrophilic polymer such as gelatin, polyvinyl alcohol, methyl cellulose and hydroxypropyl cellulose. The amount of the hydrophilic polymer is preferably 30% by weight or less, more preferably 20% by weight or less, of the total binder in the layer containing silver salt of an organic acid.

The image-forming layer generally also serves as a photosensitive layer (an emulsion layer) containing a photosensitive silver halide as a photosensitive silver salt. In that case, the weight ratio of total binder/silver halide may preferably be 5 to 400, more preferably 10 to 200.

The total amount of the binder in the image-forming layer is preferably 0.2 to 30 g/m$^2$, more preferably 1 to 15 g/m$^2$. The image-forming layer may optionally be added with a crosslinking agent, a surfactant to improve coating property of a coating solution and so forth.

The solvent for the coating solution for the image-forming layer of the photothermographic material of the present invention (for simplicity, a dispersion medium as well as a solvent is herein referred to as a "solvent") is an aqueous solvent containing at least 30% by weight of water. As components other than water, any water-miscible organic solvents may be used such as, for example, methyl alcohol, ethyl alcohol, isopropyl alcohol, methyl cellosolve, ethyl cellosolve, dimethylformamide, ethyl acetate and so forth. The water content of the solvent for the coating solution is preferably at least 50% by weight, more preferably at least 70% by weight. Preferred examples of the solvent composition include water/methyl alcohol=90/10, water/methyl alcohol=70/30, water/methyl alcohol/dimethylformamide= 80/15/5,, water/methyl alcohol/ethyl cellosolve=80/10/5, water/methyl alcohol/isopropyl alcohol=85/10/5 and so forth (numerals indicate weight %).

As a sensitizing dye that can be used for the photothermographic material of the present invention, such sensitizing dyes may advantageously be chosen which can spectrally sensitize silver halide grains within a desired wavelength range after they are adsorbed by the silver halide grains and have spectral sensitivity suitable for spectral characteristics of a light source for exposure. Sensitizing dyes and methods for addition of the dye are described in JP-A-11-65021, paragraphs 0103 to 0109; JP-A10-186572, compounds of formula (II); and EP 0803764A1, page 19, line 38 to page 20, line 35. A time to add the sensitizing dye to the silver halide emulsion may preferably be during the period after the desalting step and before coating, more preferably during the period after the desalting step and before the start of the chemical ripening.

As antifoggants, stabilizers and stabilizer precursors that can be used for the present invention, examples include, for example, those mentioned in JP-A-10-62899, paragraph 0070 and EP 0803764A1, from page 20, line 57 to page 21, line 7. Antifoggants preferably used for the present invention are organic halides. Examples thereof include, for example, those disclosed in JP-A-11-65021, paragraphs 0111 to 0112. Particularly preferred are the polyhalogenated compounds of formula (II) mentioned in JP-A-10-339934 (specific examples are tribromomethylnaphthyl-sulfone, tribromomethylphenylsulfone, tribromomethyl(4-(2,4,6-trimethylsulfonyl)-phenyl)sulfone, etc.).

The antifoggants can be formulated in the photothermographic material by the methods mentioned above as methods for formulating the reducing agents. The polyhalogenated compounds are also preferably added in the form of a solid microparticle dispersion.

Other examples of the antifoggant include the mercury(II) salts described in JP-A-11-65021, paragraph 0113 and the benzoic acids described in the same, paragraph 0114.

The photothermographic material of the present invention may contain an azolium salt as the antifoggant. Examples of the azolium salt include, for example, the compounds of the formula (XI) described in JP-A-59-193447, the compounds described in JP-B-55-12581 and the compounds of the formula (II) described in JP-A-60-153039. The azolium salt may be added in any site of the photothermographic material, and is preferably added in one or more layers on the side of an image-forming layer, more preferably in the layer containing silver salt of an organic acid. The azolium salt may be added at any time during the preparation of the coating solution. When the azolium salt is added to the layer containing silver salt of an organic acid, the azolium salt may be added at any time during the period of from the preparation of the silver salt of an organic acid to the preparation of the coating solution. A time during the period after the preparation of the silver salt of an organic acid and just before coating is preferred. The azolium salt may be added as any form such as powder, a solution, and a microparticle dispersion. The salt may also be added as a solution prepared by mixing the salt with other additives such as a sensitizing dye, a reducing agent, and a color tone adjuster. In the present invention, the amount of the azolium salt to be added is not particularly limited, and the amount may preferably be $1 \times 10^{-6}$ mole to 2 moles, more preferably $1 \times 10^{-3}$ mole to 0.5 mole, per mole of silver.

The photothermographic material of the invention may optionally contain a mercapto compound, a disulfide compound, and a thione compound to accelerate, suppress, or control development, or increase efficiency in spectral sensitivity, or to improve storability before and after development. Examples include, for example, those described in JP-A-10-62899, paragraphs 0067 to 0069, compounds of the formula (I) and specific examples in the paragraphs 0033 to 0052 of JP-A-10-186572, and those described in EP 0803764A1, page 20, lines 36 to 56. Among them, mercapto-substituted heteroaromatic compounds are preferred.

In the photothermographic material of present invention, it is preferable to add a toning agent. Examples of the toning agent are described in JP-A-10-62899, paragraphs 0054 to 0055 and EP 0803764A1, page 21, lines 23 to 48. Preferred examples include phthalazinone, phthalazinone derivatives (e.g., 4-(1-naphthyl)phthalazinone, 6-chlorophthalazinone, 5,7-dimethoxyphthalazinone, 2,3-dihydro-1,4-phthalazinone and other derivatives) and metal salts thereof; combinations of phthalazinones and phthalic acid or derivatives thereof (e.g., phthalic acid, 4-methylphthalic acid, 4-nitrophthalic acid, tetrachlorophthalic anhydride and so forth); phthalazines including phthalazine and phthalazine derivatives (e.g., 4-(1-naphthyl)phthalazine, 6-isopropylphthalazine, 6-t-butylphthalazine, 6-chlorophthalazine, 5,7-dimethoxyphthalazine, 2,3-dihydrophthalazine and other derivatives) and metal salts thereof; combinations of phthalazines and phthalic acid or derivatives thereof (e.g., phthalic acid, 4-methylphthalic acid, 4-nitrophthalic acid, tetrachlorophthalic anhydride and so forth). Particularly preferred examples include the combinations of phthalazines and phthalic acid or derivatives thereof.

Plasticizers and lubricants may be used in the photothermographic material of the present invention, and these agents are described in JP-A-11-65021, paragraph 0117. Ultrahigh contrast agents for forming ultrahigh contrast images are described in the same publication, paragraph 0118 and those compounds mentioned in Japanese Patent Application No. 11-91652 as compounds of the general formulas (III) to (V) (specific compounds: Chem. 21 to Chem 24); and hardness enhancement promoters are described in JP-A-11-65021, paragraph 0102. Those can be formulated in the photothermographic material.

The photothermographic material of the present invention may be provided with a surface protective layer, for example, to prevent adhesion of the image-forming layer. The surface protective layer is described in, for example, JP-A-11-65021, paragraphs 0119 to 0120.

Gelatin is preferred as the binder in the surface protective layer, and polyvinyl alcohol (PVA) is also preferably used. Examples of PVA includes, for example, completely saponified PVA-105 [having a polyvinyl alcohol (PVA) content of at least 94.0% by weight, a degree of saponification of 98.5±0.5 mole %, a sodium acetate content of 1.5% by weight or less, a volatile content of 5.0% by weight or less, a viscosity (4% by weight at 20° C.) of 5.6±0.4 CPS]; partially saponified PVA-205 [having a PVA content of 94.0% by weight, a degree of saponification of 88.0±1.5 mole %, a sodium acetate content of 1.0% by weight, a volatile content of 5.0% by weight, a viscosity (4% by weight at 20° C.) of 5.0±0.4 CPS]; modified polyvinyl alcohols, MP-102, MP-202, MP-203, R-1130, R2105 (all from Kraray) and so forth. The application amount of the polyvinyl alcohol (per m² of the support) for protective layers is preferably 0.3 to 4.0 g/m², more preferably 0.3 to 2.0 g/m² (per one layer).

The temperature for preparation of the coating solution for the image-forming layer may preferably be 30° C. to 65° C., more preferably 35° C. to 60° C., further preferably 35° C. to 55° C. The temperature of the coating solution immediately after the addition of the polymer latex may preferably be kept at 30° C. to 65° C. A reducing agent and a silver salt of an organic acid may preferably be mixed before the addition of polymer latex.

The coating solution for the image-forming layer is preferably a so-called thixotropic flow. Thixotropy means that viscosity of a fluid lowers with increase of shear rate. Any apparatus may be used for measurement of viscosity, and for example, RFS Fluid Spectrometer from Rheometrics Far East Co., Ltd. is preferably used and the measurement is performed at 25° C. Viscosity of the coating solution for the image-forming layer is preferably 400 mPa·s to 100,000 mPa·s, more preferably 500 mPa·s to 20,000 mPa·s, at a shear rate of 0.1 sec$^{-1}$. The viscosity is preferably 1 mPa·s to 200 mPa·s, more preferably 5 mPa·s to 80 mPa·s, at a shear rate of 1000 sec$^{-1}$.

Various systems exhibiting thixotropic property are known and, for example, described in "Lecture on Rheology", Kobunshi Kanko Kai; Muroi & Morino, "Polymer Latex", Kobunshi Knako Kai and so forth. A fluid is required to contain a large amount of fine solid microparticles to exhibit thixotropic property. For enhancing thixotropic property, it is effective that the fluids is added with a viscosity-increasing linear polymer, or fine solid microparticles to be contained have anisotropic shapes and an increased aspect ratio. Use of an alkaline viscosity-increasing agent or a surfactant is also effective for that purpose.

The image-forming layer is formed as one or more layers on the support, and contains a silver salt of an organic acid. It may also contain desired additional materials such as photosensitive silver halide, reducing agent, binder, toning agent, coating aid and other auxiliary agents. When the layer is monolayer, the layer preferably contains a silver salt of an organic acid, photosensitive silver halide, reducing agent and binder. When the layer is bilayer, the first emulsion layer (in general, the layer adjacent to the support) may contain a silver salt of an organic acid and photosensitive silver halide, and the second emulsion layer or said two layers may contain the other ingredients. Another type of bilayer structure is also employable in which one layer is a single emulsion layer containing all necessary ingredients and the other layer is a protective top coat layer. Multicolor photothermographic material may contain these two layers for each color, or may contain all necessary ingredients in a single layer as described in U.S. Pat. No. 4,708,928. As for multicolor photothermographic materials containing multiple dyes, each emulsion layers are kept distinguished by using a functional or non-functional barrier layer between the adjacent photosensitive layers as described in U.S. Pat. No. 4,460,681.

In the image-forming layer, various types of dyes and pigments may be used to improve color tone, to prevent interference fringes generated during laser exposure, and to prevent irradiation. These techniques are detailed in WO98/36322. Preferred dyes and pigments for the photothermographic material of the present invention include, for example, anthraquinone dyes, azomethine dyes, indoaniline dyes, azo dyes, indanthrone pigments of anthraquinone type (e.g., C.I. Pigment Blue 60 and so forth), phthalocyanine pigments (e.g., copper phthalocyanines such as C.I. Pigment Blue 15; metal-free pbthalocyanines such as C.I. Pigment Blue 16); triarylcarbonyl pigments of printing lake pigment type, indigo, inorganic pigments (e.g., ultramarine, cobalt blue and so forth). Any methods are employed to add these dyes and pigments such as addition as a solution, an emulsion, or a dispersion of fine solid microparticles, or addition of those mordanted by using a polymer mordant. The amount of these compounds to be used may vary depending on intended absorbance. Generally, the compounds may preferably be in an amount of 1 $\mu$g to 1 g per $m^2$ of the photothermographic material.

In the photothermographic material of the invention, an antihalation layer may be provided in a distant position from a light source relative to the image-forming layer. The antihalation layer is described in JP-A-11-65021, paragraphs 0123 to 0124.

In the photothermographic material of the present invention, a decoloring dye and a base precursor are preferably added to a non-image-forming layer of the photothermographic material so that the non-image-forming layer can function as a filter layer or an antihalation layer. Photothermographic materials generally have non-image-forming layers in addition to the image-forming layers. Depending on their positions, the non-image-forming layers are classified into (1) a protective layer to be provided on an image-forming layer (the opposite side of the support); (2) an intermediate layer to be provided between two or more of image-forming layers or between an image-forming layer and a protective layer; (3) an undercoat layer to be provided between an image-forming layer and a support; (4) a backing layer to be provided on a side opposite to the image-forming layer. The filter layer is provided in the photosensitive material as the layer (1) or (2). The antihalation layer is provided in the photosensitive material as the layer (3) or (4).

The decoloring dye and the base precursor are preferably added to the same non-image-forming layer. They may be also added separately to adjacent two non-image-forming layers. If desired, a barrier layer may be provided between the two non-image-forming layers.

As methods to add a decoloring dye to a non-image-forming layer, a method may be employed which comprises step of adding a solution, an emulsion, a solid microparticles dispersion of the dye, or the dye impregnated with a polymer to a coating solution for the non-image-forming layer. The dye may also be added to the non-image-forming layer by using a polymer mordant. These methods for addition are the same as those generally employed for the addition of dyes to ordinary photothermographic materials. Polymer latexes used for preparation of the dye impregnated with a polymer are described in U.S. Pat. No. 4,199,363, German Patent Laid-open Nos. 25,141,274, 2,541,230, EP-A-029104, and JP-B-53-41091. A method for emulsification by adding a dye to a solution in which a polymer is dissolved is described in International Patent Publication WO88/00723.

The amount of the decoloring dye may be determined depending on purpose of the use of the dye. In general, the dye:is used in an amount to give an optical density (absorbance) of larger than 1.0 measured at an intended wavelength. The optical density is preferably 0.2 to 2. The amount of the dye to give such optical density may be generally from about 0.001 to about 1 $g/m^2$, particularly preferably from about 0.01 to about 0.2 $g/m^2$.

Decoloring of dyes in that manner can lower optical density of the material to 0.1 or less. Two or more different decoloring dyes may be used in the thermodecoloring type recording materials or photothermographic materials. Similarly, two or more different base precursors may be used in combination.

The photothermographic material of the present invention is preferably a so-called single-sided photosensitive material comprising at least one image-forming layer containing a silver halide emulsion on one side of support, and a backing layer on the other side.

The photothermographic material of the present invention may preferably contain a matting agent for improving the transferability of the material. Matting agents are described in JP-A-11-65021, paragraphs 0126 to 0127. The matting agent is added in an amount of preferably 1 to 400 $mg/m^2$, more preferably 5 to 300 $mg/m^2$ as the amount per 1 $m^2$ of the photosensitive material.

The matting degree of the surface of the emulsion layer is not particularly limited so long as the material is free from stardust defects. Beck's smoothness of the matted surface is preferably 30 seconds to 2000 seconds, more preferably 40 seconds to 1500 seconds.

The matting degree of the backing layer in the present invention is preferably falls 10 seconds to 1200 seconds, more preferably 20 seconds to 800 seconds, most preferably 40 seconds to 500 seconds as shown by the Beck's smoothness.

The matting agent may preferably be contained in the outermost surface layer, or in a layer functioning as an outermost surface layer, or in a layer near to the outer surface of the photothermographic material. The agent may also be preferably contained in a layer functioning as a protective layer.

The backing layers that are applicable to the photothermographic material of the present invention are described in JP-A-11-65021, paragraphs 0128 to 0130.

A hardening agent may be added to the image-forming layer, the protective layer, the backing layer, and other layers. Examples of the hardening agent are described in T. H. James, "THE THEORY OF THE PHOTOGRAPHIC PROCESS, FOURTH EDITION", Macmillan Publishing Co., Inc., 1977, pp. 77–87. Polyvalent metal ions described on page 78 of the above article, polyisocyanates described in U.S. Pat. No. 4,281,060 and JP-A-6-208193; epoxy compounds described in U.S. Pat. No. 4,791,042; vinylsulfone compounds described in JP-A-62-89048 and so forth may preferably be used.

The hardening agent is added to coating solutions as a solution. Preferred addition time of the solution to the coating solution of the protective layer resides in a period of from 180 minutes before the coating to just before the coating, preferably 60 minutes to 10 seconds before the coating. The method and conditions for mixing are not particularly limited as far that the effect of the present invention can be obtained satisfactorily. Specific examples of the mixing method include a method in which a mixing is performed in a tank designed so as to obtain a desired average residence time which is calculated from addition flow rate and feeding amount to a coater, a method utilizing a static mixer described in N. Harnby, M. F. Edwards, A. W. Nienow, "Ekitai Kongo Gijutsu (Techniques for Mixing Liquids)", translated by Koji Takahashi, Chapter 8, Nikkan Kogyo Shinbunsha, 1989 and so forth.

Surfactants that can be used in the present invention are described in JP-A-11-65021, paragraph 0132; usable solvents are described in the above patent document in paragraph 0133; usable supports are described in the above patent document in paragraph 0134; usable antistatic and electroconductive layers are described in the above patent document in paragraph 0135; and usable methods for forming color images are described in the above patent document in paragraph 0136.

A transparent support for the photothermographic material of the present invention may be colored with a blue dye (e.g., with Dye-1 described in Examples of JP-A-8-240877) or may be colorless. Techniques for undercoating the support are described in JP-A-11-84574, JP-A-10-186565 and so forth. For the antistatic layer and undercoating, the techniques mentioned in JP-A-56-143430, JP-A-56-143431, JP-A-58-62646, JP-A-56-120519 and so forth can also be used.

The photothermographic material is preferably a monosheet type material (which means a type of material in which no additional sheet is used for image receiving materials, and can form images directly on the material itself).

The photothermographic material may further contain an antioxidant, a stabilizer, a plasticizer, a ultraviolet absorber or a coating aid. Such additives may be added to any of image-forming layers or non-image-forming layers. For these additives, WO98/36322, EP803764A1, JP-A-10-186567, JP-A-10-18568 and so forth may be referred to.

The coating method for the preparation of the photothermographic material is not particularly limited, and any coating methods may be employed. Specific examples thereof include various types of coating techniques, for example, extrusion coating, slide coating, curtain coating, dip coating, knife coating, flow coating, extrusion coating utilizing a hopper of the type described in U.S. Pat. No. 2,681,294 and so forth. Preferred examples include extrusion coating and slide coating described in Stephen F. Kistler, Petert M. Schweizer, "LIQUID FILM COATING", published by CHAPMAN & HALL Co., Ltd., 1997, pp.399–536, and a most preferable example includes the slide coating. An example of the shape of a slide coater used for the slide coating is shown in FIG. 11b, 1, on page 427 of the aforementioned reference. If desired, two or more layers may be formed at the same time, for example, according to the methods described from page 399 to page 536 of the aforementioned reference, or the methods described in U.S. Pat. No. 2,761,791 and British Patent No. 837,095.

Other techniques that can be used for the production of the photothermographic material of the present invention are also described in
EP803764A1, EP883022A1, WO98/36322, JP-A-56-62648, JP-A-58-62744,
JP-A-9-281637, JP-A-9-297367, JP-A-9-304869, JP-A-9-311405, JP-A-9-329865,
JP-A-10-10669, JP-A-10-62899, JP-A-10-69023, JP-A-10-186568, JP-A-10-90823,
JP-A-10-171063, JP-A-10-186565, JP-A-10-186567, JP-A-10-186569, JP-A-10-186570,
JP-A-10-186571, JP-A-10-186572, JP-A-10-197974, JP-A-10-197982, JP-A-10-197983,
JP-A-10-197985, JP-A-10-197986, JP-A-10-197987, JP-A-10-207001, JP-A-10-207004,
JP-A-10-221807, JP-A-10-282601, JP-A-10-288823, JP-A-10-288824, JP-A-10-307365,
JP-A-10-312038, JP-A-10-339934, JP-A-11-7100, JP-A-11-15105, JP-A-11-24200,
JP-A-11-24201, JP-A-11-30832, JP-A-11-84574, JP-A-11-65021, JP-A-11-125880,
JP-A-11-129629, JP-A-11-133536, JP-A 11-133537, JP-A-11-133538, JP-A-11-133539,
JP-A-11-133542-and JP-A-11-133543.

The photothermographic material of the invention may be developed in any manner. Usually, an imagewise exposed photothermographic material is developed by heating. The temperature for the development is preferably 80° C. to 250° C., more preferably 100° C. to 140° C. The development time is preferably 1 to 180 seconds, more preferably 10 to 90 seconds, most preferably 10 to 40 seconds.

For thermal development for the material, a plate heater system is preferred. For heat development by the plate heater system, the methods described in Japanese Patent Application Nos. 9-229684 and, 10-177610 are preferred, which can use a heat development apparatus wherein a photothermographic material on which a latent image is formed is brought into contact with a heating means in a heat development section to obtain a visible image, and wherein the heating means comprises a plate heater, and a plurality of presser rollers are disposed facing to one surface of the plate heater, and wherein heat development of the photothermographic material is attained by passing the material between the presser rollers and the plate heater. The plate heater is preferably sectioned into 2 to 6 stages, and the temperature of the top stage is preferably kept lower by approximately 1 to 10° C. than that of the others stages. Such a method is also described in JP-A-54-30032. The plate heater system can remove moisture and organic solvent contained in the photothermographic material out of the material, and prevent change in shape of the support of the photothermographic material by rapid heating of the material.

The photothermographic material of the present invention can be exposed by any means. As light source of exposure, laser rays are preferred. As the laser used in the present invention, gas lasers ($Ar^+$, He—Ne), YAG lasers, dye lasers, semiconductor lasers and so forth are preferred. A combination of semiconductor laser and second harmonic generating device may also be used. Preferred examples include gas and semiconductor lasers for red to infrared emission.

Single mode lasers can be used as the laser rays, and the technique disclosed in JP-A-11-65021, paragraph 0140, can be used.

The laser output is preferably at least 1 mW, more preferably at least 10 mW. Even more preferred is high output of at least 40 mW. If desired, a plurality of lasers may be combined. The diameter of a laser beam may be between about 30 and 200 $\mu$m based on the level of $1/e^2$ spot size of a Gaussian beam.

An example of a laser imager provided with a light exposure section and a heat development section is Fuji Medical Dry Laser Imager FM-DP L.

The photothermographic materials of the present invention form a monochromatic image based on silver image, and are preferably used as photothermographic materials for use in medical diagnosis, industrial photography, printing and COM. It should be understood that, in such applications, the monochromatic images formed can be duplicated on duplicating films, MI-Dup, from Fuji Photo Film for medical diagnosis, and for printing, the images can be used as a mask for forming reverse images on printing films such as DO-175 and PDO-100 from Fuji Photo Film, or on offset printing plates.

EXAMPLES

The present invention will be specifically explained with reference to the following examples. However, the scope of the present invention is not limited to the following examples.

Example 1

(Preparation of PET Support)

Using terephthalic acid and ethylene glycol, PET having an intrinsic viscosity IV of 0.66 (measured in phenol/tetrachloroethane=6/4 (weight ratio) at 25° C.) was obtained in a conventional manner. The PET was pelletized, and the pellets were dried at 130° C. for 4 hours, melted at 300° C., extruded from a T-die, and quenched to prepare an unstretched film having a thickness of 175 µm after thermal fixation.

The film was stretched along the longitudinal direction by 3.3 times using rollers having different peripheral speeds and then stretched along the transverse direction by 4.5 times using a tenter. In these processes, the temperatures were 110° C. and 130° C., respectively. The film was then subjected to thermal fixation at 240° C. for 20 seconds and relaxed by 4% along the transverse direction at the same temperature. Then, after chucks of the tenter were released, the both edges of the film were knurled, and the film was rolled up at 4 kg/cm² to provide a roll of the film having a thickness of 175 µm.

(Surface Corona Discharging Treatment)

Using a solid state corona discharging treatment machine Model 6KVA manufactured by Piller Inc., both surfaces of the support were treated at room temperature at 20 m/minute. From the read out values of the electric current and voltage, it was found that the treatment of 375 kV·A·minute/m² was applied to the support in the process. The treated frequency in the process was 9.6 kHz and the gap clearance between the electrode and the dielectric roll was 1.6 mm.

(Preparation of Undercoated Support)

(1) Preparation of Coating Solution for Undercoat Layer

| Formulation (1) (for undercoat layer on photosensitive layer side) | |
|---|---|
| Pesresin A-515GB made by Takamatsu Yushi K. K. (30 weight % solution) | 234 g |
| Polyethylene glycol mononylphenyl ether (mean ethylene oxide number = 8.5, 10 weight % solution) | 21.5 g |
| MP-1000 made by Soken Kagaku K. K. (polymer microparticles, mean particle size: 0.4 µm) | 0.91 g |
| Distilled water | 744 ml |

| -continued | |
|---|---|
| Formulation (2) (for 1st layer on back surface) | |
| Butadiene-styrene copolymer latex (solid content: 40% by weight, weight ratio of butadiene/styrene = 32/68) | 158 g |
| 2,4-Dichloro-6-hydroxy-S-triazine sodium salt (8 weight % aqueous solution) | 20 g |
| 1 weight % Aqueous solution of sodium laurylbenzenesulfonate | 10 ml |
| Distilled water | 854 ml |
| Formulation (3) (for 2nd layer on back surface side) | |
| $SnO_2$/SbO (weight ratio: 9/1, mean particle size: 0.038 µm, 17 weight % dispersion) | 84 g |
| Gelatin (10% aqueous solution) | 89.2 g |
| Metorose TC-5 made by Shin-Etsu Chemical Co., Ltd. (2% aqueous solution) | 8.6 g |
| MP-1000 (polymer microparticles) made by Soken Kagaku K. K. | 0.01 g |
| 1 weight % Aqueous solution of sodium dodecylbenzenesulfonate | 10 ml |
| NaOH (1%) | 6 ml |
| Proxel (made by ICI Co.) | 1 ml |
| Distilled water | 805 ml |

(Preparation of Undercoated Support)

After application of the aforementioned corona discharging treatment to both surfaces of the aforementioned biaxially stretched polyethylene terephthalate support having a thickness of 175 µm, one surface (photosensitive layer coating surface side) thereof was coated with the undercoating solution of Formulation (1) by a wire bar in a wet coating amount of 6.6 ml/m² (per one surface) and dried at 180° C. for 5 minutes. Then, the back surface thereof was coated, with the undercoating solution of Formulation (2) by a wire bar in a wet coating amount of 5.7 ml/m² and dried at 180° C. for 5 minutes. Further, the back surface thus coated was coated with the undercoating solution of Formulation (3) by a wire bar in a wet coating amount of 7.7 ml/m² and dried at 180° C. for 6 minutes to prepare an undercoated support.

(Preparation of Coating Solution for Back Surface)

(Preparation of Solid Microparticle Dispersion (a) of Base Precursor)

64 g of Base precursor compound 11, 28 g of diphenylsulfone and 10 g of a surface active agent, Demor N (manufactured by Kao Corporation), were mixed with 220 ml of distilled water, and the mixture was beads-dispersed using a sand mill (¼ Gallon Sand Grinder Mill, manufactured by Imex Co.) to obtain Solid microparticle dispersion (a) of the base precursor compound having a mean particle size of 0.2 µm.

(Preparation of Dye Solid Microparticle Dispersion)

9.6 g of Cyanine dye compound 13 and 5.8 g of sodium p-dodecylbenzenesulfonate were mixed with 305 ml of distilled water and the mixture was beads—dispersed using a sand mill (¼ Gallon Sand Grinder Mill, manufactured by Imex Co.) to obtain a dye solid mnicroparticle dispersion having a mean particle size of 0.2 µm.

(Preparation of Coating Solution for Antihalation Layer)

17 g of gelatin, 9.6 g of polyacrylamide, 70 g of the aforementioned Solid microparticle dispersion (a) of the base precursor, 56 g of the aforementioned dye solid microparticle dispersion, 1.5 g of polymethyl methacrylate microparticles (mean particle size 6.5 µm), 0.03 g of benzoisothiazolinone, 2.2 g of sodium polyethylenesulfonate, 0.2 g of Blue dye compound 14 and 844 ml of water were mixed to prepare a coating solution for antihalation layer.

(Preparation of Coating Solution for Back Surface Protective Layer)

In a container kept at 40° C., 50 g of gelatin, 0.2 g of sodium polystyrenesulfonate, 2.4 g of N,N-ethylenebis(vinylsulfonacetamide), 1 g of sodium t-octylphenoxyethoxyethanesulfonate, 30 mg of benzoisothiazolinone, 37 mg of N-perfluorooctylsulfonyl-N-propylalanine potassium salt, 0.15 g of polyethyleneglycol mono-(N-perfluorooctylsulfonyl-N-propyl-2-aminoethyl) ether [average polymerization degree of ethylene oxide: 15], 32 mg of $C_8F_{17}SO_3K$, 64 mg of $C_8F_{17}SO_2N(C_3H_7)$-$(CH_2CH_2O)_4$-$(CH_2)_4$-$SO_3Na$, 8.8 g of an acrylic acid/ethyl acrylate copolymer (copolymerization ratio (by weight): 5/95), 0.6 g of Aerosol OT (manufactured by American Cyanamid Company), 1.8 g (as liquid paraffin) of a liquid paraffin emulsion and 950 ml of water were mixed to form a coating solution for a back surface protective layer.

(Preparation of Silver Halide Emulsion 1)

1421 ml of distilled water was added with 8.0 ml of a 1% by weight potassium bromide solution, and further added with 8.2 ml of 1 N nitric acid and 20 g of phthalized gelatin. Separately, Solution A was prepared by adding distilled water to 37.04 g of silver nitrate to dilute it to 159 ml, and Solution B was prepared by diluting 32.6 g of potassium bromide with distilled water to a volume of 200 ml. To the aforementioned mixture maintained at 37° C. and stirred in a titanium-coated stainless steel reaction vessel, the whole volume of Solution A was added by the control double jet method over 1 minute at a constant flow rate while pAg was maintained at 8.1. Solution B was also added by the control double jet method. Then, the mixture was added with 30 ml of 3.5 weight % aqueous hydrogen peroxide solution, and further added with 36 ml of a 3% by weight aqueous solution of benzimidazole. Separately, Solution A2 was prepared by diluting Solution A with distilled water to a volume of 317.5 ml, and Solution B2 was prepared by dissolving tripotassium hexachloroiridate in Solution B to obtain final concentration of $1 \times 10^{-4}$ mole per mole of silver, and diluting the obtained solution with distilled water to a volume twice as much as the volume of Solution B, i.e., 400 ml. The whole volume of Solution A2 was added to the mixture again by the control double jet method over 10 minutes at a constant flow rate while pAg was maintained at 8.1. Solution B2 was also added by the control double jet method. Then, the mixture was added with 50 ml of a 0.5% by weight solution of 5-methyl-2-mercaptobenzimidazole in methanol. After pAg was raised to 7.5 with silver nitrate, the mixture was adjusted to pH 3.8 using 1 N sulfuric acid, and the stirring was stopped. Then, the mixture was subjected to precipitation, desalting and washing with water, added with 3.5 g of deionized gelatin and 1 N sodium hydroxide to be adjusted to pH 6.0 and pAg of 8.2 to form a silver halide dispersion.

The grains in the resulting silver halide emulsion were pure silver bromide grains having a mean spherical diameter of 0.053 μm and a variation coefficient of 18% in terms of spherical diameter. The grain size and others were obtained from averages for 1000 grains by using an electron microscope. The [100] face ratio of these grains was determined to be 85% by the Kubelka-Munk method.

The aforementioned emulsion was added with 0.035 g of benzoisothiazolinone (added as a 3.5 weight % methanol solution of the compound) with stirring at 38° C., and after 40 minutes, the mixture was added with the solid dispersion (an aqueous gelatin solution) of Spectral sensitizing dye A in an amount of $5 \times 10^{-3}$ mole per mole of silver. After 1 minutes, the mixture was warmed to 47° C., and after 20 minutes, added with $3 \times 10^{-5}$ mole of sodium benzenethiosulfonate per mole of silver. Further after 2 minutes, the mixture was added with Tellurium sensitizer B in an amount of $5 \times 10^{-5}$ mole per mole of silver followed by ripening for 90 minutes. Immediately before completion of the ripening, the mixture was added with 5 ml of a 0.5 weight % methanol solution of N,N'-dihydroxy-N"-diethylmelamine. After the temperature was lowered to 31° C., the mixture was added with 5 ml of a 3.5% by weight methanol solution of phenoxyethanol, $7 \times 10^{-3}$ mole of 5-methyl-2-mercaptobenzimidazole per mole of silver, and $6.4 \times 10^{-3}$ mole of 1-phenyl-2-heptyl-5-mercapto-1,3,4-triazole per mole of silver to prepare Silver halide emulsion 1.

(Preparation of Silver Halide Emulsion 2)

In the same manner as the preparation of Silver halide emulsion 1 except that the liquid temperature for forming the grains was changed from 37° C. to 50° C., a pure silver bromide cubic grain emulsion having a mean grain size of 0.08 μm as spheres and a variation coefficient of 15% for size as spheres was prepared. Further, as in the case of Silver halide emulsion 1, the steps of precipitation, desalting, washing with water and dispersion were performed. Furthermore, in the same manner as in the case of Silver halide emulsion 1 except that the addition amount of Spectral sensitizing dye A was changed to $4.5 \times 10^{-3}$ mole per mole of silver, the spectral sensitization, the chemical sensitization, and addition of 5-methyl-2-mercaptobenzimidazole and 1-phenyl-2-heptyl-5-mercapto-1,3,4-triazole were performed to obtain Silver halide emulsion 2.

(Preparation of Silver Halide Emulsion 3)

In the same manner as the preparation of Silver halide emulsion 1 except that the liquid temperature for forming the grains was changed from 37° C. to 27° C., a pure silver bromide cubic grain emulsion having a mean grain size of 0.038 μm as spheres and a variation coefficient of 20% for size as spheres was prepared. Further, as in the case of Silver halide emulsion 1, the steps of precipitation, desalting, washing with water and dispersion were performed. Furthermore, in the same manner as in the case of Silver halide emulsion 1 except that the addition amount of Spectral sensitizing dye A was changed to $6 \times 10^{-3}$ mole per mole of silver, the spectral sensitization, the chemical sensitization, and the addition of 5-methyl-2-mercaptobenzimidazole and 1-phenyl-2-heptyl-5-mercapto-1,3,4-triazole were performed to obtain Silver halide emulsion 3.

(Preparation of Mixed Emulsion 1-A for Coating Solution)

70% by weight of Silver halide emulsion 1, 15% by weight of Silver halide emulsion 2 and 15% by weight of Silver halide emulsion 3 were mixed and added with benzothiazolium iodide in an amount of $7 \times 10^{-3}$ mole per mole of silver as a 1% by weight aqueous solution to form Mixed emulsion 1-A for coating solution.

(Preparation of Comparative Organic Acid Silver Salt 1)

87.6 kg of behenic acid (Edenor C22-85R, trade name, manufactured by Henkel Co.), 423 L of distilled water, 49.2 L of a 5 N aqueous solution of NaOH, and 120 L of tert-butanol were mixed and reacted with stirring at 75° C. for one hour to obtain a solution of sodium behenate. Separately, 206.2 L of an aqueous solution containing 40.4 kg of silver nitrate (pH 4.0) was prepared and kept at 10° C. A mixture of 635 L of distilled water and 30 L of tert-butanol contained in a reaction vessel kept at 30° C. was added with the whole amount of the aforementioned sodium behenate solution and the whole amount of the aqueous silver nitrate solution at constant flow rates over the periods of 62 minutes and 10 seconds, and 60 minutes, respectively. In this procedure, the solutions were added in such a manner that only the aqueous silver nitrate solution was added for 7 minutes and 20 seconds after starting the addition of the aqueous silver nitrate solution, and for 9 minutes and 30 seconds after finishing the addition of the aqueous silver nitrate solution, only the sodium behenate solution was added. In this operation, the outside temperature was controlled to adjust the temperature in the reaction vessel at 30° C. and keep the liquid temperature constant. The piping of the addition system for the sodium behenate solution was heated by steam trace and the steam opening was controlled to adjust the liquid temperature at the outlet orifice of the addition nozzle at 75° C. The piping of the addition system for the aqueous silver nitrate solution was kept cooled by circulating cold water outside a double pipe. The addition position of the sodium behenate solution and the addition position of the aqueous silver nitrate solution were arranged symmetrically relative to the stirring axis at the center, and the positions are controlled at heights not to contact with the reaction mixture.

After completion of the addition of the sodium behenate solution, the mixture was left with stirring for 20 minutes at the same temperature and then the temperature was lowered to 25° C. The solid content was then recovered by a suction filtration and the solid content was washed with water until the electric conductivity of the filtrate became 30 $\mu$S/cm. Thus, a fatty acid silver salt was obtained. The solid content was stored as a wet cake without being dried.

To the wet cake corresponding to 100 g of the dry solid content was added with 7.4 g of polyvinyl alcohol (PVA-217, trade name) and water to make the total amount 385 g, and the mixture was pre-dispersed by a homomixer.

Then, the pre-dispersed stock dispersion was treated three times by using a dispersing machine (Microfluidizer M-110S-EH; trade name, manufactured by Microfluidex International Corporation, using G10Z interaction chamber) with a pressure controlled to 1750 kg/cm$^2$ to obtain a silver behenate dispersion. During the cooling operation, a dispersion temperature of 18° C. was achieved by providing coiled heat exchangers fixed before and after the interaction chamber and controlling the temperature of the refrigerant.

When the shape of the obtained silver behenate grains was evaluated by an electron microscopic photography, the grains were scaly crystals having a=0.14 $\mu$m, b=0.4 $\mu$m, and c=0.6 $\mu$m in mean values, a mean aspect ratio of 5.2, a mean diameter as spheres of 0.52 $\mu$m, and a variation coefficient of 15% for mean diameter as spheres (a, b and c have the meanings defined in the present specification).

(Preparation of Comparative Organic Acid Silver Salt 2)

Organic acid silver salt 2 was prepared in exactly the same manner as that for Comparative organic acid silver salt 1 except that the aqueous solution added to a reaction vessel beforehand (635 L of distilled water and 30 L of t-butanol) was changed to an aqueous solution containing 551 L of distilled water, 30 L of t-butanol, and 88 kg of 10 weight % aqueous solution of naphthalenesulfonate polymer having an average molecular weight of 100,00, and the suction filtration was replaced with ultrafiltration. When the shape of the obtained silver behenate grains was evaluated by an electron microscopic photography, the grains were rod-like crystals having a mean diameter as spheres of 0.15 $\mu$m, and a variation coefficient of 21% for mean diameter as spheres.

(Ultrafiltration)

Each of the obtained organic acid silver salt dispersions was subjected to desalting treatment by transferring the dispersion to an ultrafiltration apparatus shown in FIG. 1. The ultrafiltration apparatus was basically constituted by a tank 1 for stocking the organic acid silver salt dispersion, and a circulation pump 2 for feeding the stocked dispersion to an ultrafiltration module 3, and provided with a flowmeter 4 for measuring flow rate of supplemental pure water, a flowmeter 5 for measuring amount of permeated water, a pump 6 for washing in reverse direction, and so forth. The membrane module used was a hollow yarn type one, ACP-1050, produced by Asahi Chemical Industry Co., Ltd. The feeding flow rate was 18 L/minute, and the pressure difference before and after the module was 1.0 kg/cm$^2$.

The established condition was maintained by continuously monitoring pH even during the desalting treatment. 1N NaOH and HNO$_3$ were used for pH adjustment. The pH adjustment was stopped when the conductivity became less than 1000 $\mu$S/cm. Further, the supplementation of pure water was stopped when the conductivity was decreased to 50 $\mu$S/cm, and the dispersion was concentrated to a concentration of 26% by weight. The solid concentration was measured by using a digital specific gravimeter Model DA-300, produced by Kyoto Denshi Co., Ltd., and the definitive content was determined from the absolute dry weight.

(Preparation of Organic Acid Silver Salt Dispersion 1-A of the Present Invention)

Organic acid silver salt dispersion 1-A was prepared in exactly the same manner as that for Comparative organic acid silver salt 2 except that the aqueous solution added to a reaction vessel beforehand was changed to an aqueous solution containing 551 L of distilled water, 30 L of t-butanol, and 44 kg of 10 weight % aqueous solution of sodium tetradecane 2,3-ene-1-sulfonate (molecular weight: 299).

When the shape of the obtained silver behenate grains was evaluated by an electron microscopic photography, the grains were scaly crystals having a mean diameter as spheres of 0.5 $\mu$m, and a variation coefficient of 10% for mean diameter as spheres.

(Preparation of Inventive Organic Acid Silver Salt Dispersion 1-B)

Organic acid silver salt dispersion 1-B was prepared in exactly the same manner as that for Organic acid silver salt dispersion 1-A except that the surfactant of the aqueous solution added to a reaction vessel was changed to a 10% by weight aqueous solution of triisopropylnaphthalenesulfonic acid (molecular weight: 357). When the shape of the obtained silver behenate grains was evaluated by an electron microscopic photography, the grains were rod-like crystals having a mean diameter as spheres of 0.47 $\mu$m, and a variation coefficient of 11% for mean diameter as spheres.

(Preparation of Inventive Organic Acid Silver Salt Dispersion 1-C)

Organic acid silver salt dispersion 1-C was prepared in exactly the same manner as that for Organic acid silver salt dispersion 1-A except that the surfactant of the aqueous solution added to a reaction vessel was changed to a 10% by weight aqueous solution of naphthalenesulfonic acid oligomer (average molecular weight: 1250). When the shape of the obtained silver behenate grains was evaluated by an electron microscopic photography, the grains were scaly crystals having a mean diameter as spheres of 0.53 $\mu$m, and a variation coefficient of 14% for mean diameter as spheres.

(Preparation of 25 Weight % Dispersion of Reducing Agent)

10 kg of 1,1-bis(2-hydroxy-3,5-dimethylphenyl)-3,5,5-trimethylhexane and 10 kg of a 20 weight % aqueous solution of denatured polyvinyl alcohol (Poval MP203, manufactured by KURARAY CO., LTD.) were added with 16 kg of water, and mixed sufficiently to form a slurry. The slurry was fed by a diaphragm pump to a sand mill of horizontal type (UVM-2, manufactured by Imex Co.) containing zirconia beads having a mean diameter of 0.5 mm, and dispersed for 3 hours and 30 minutes. Then, the slurry was added with 0.2 g of benzothiazolinone sodium salt and water to adjust the concentration of the reducing agent to 25% by weight to obtain a reducing agent dispersion. The reducing agent particles contained in the reducing agent dispersion obtained as described above had a median diameter of 0.42 $\mu$m and the maximum particle size of 2.0 $\mu$m or shorter. The obtained reducing agent dispersion was filtered through a polypropylene filter having a pore size of 10.0 $\mu$m to remove insoluble solids such as dusts, and then stored.

(Preparation of 10 Weight % Dispersion of Mercapto Compound)

5 kg of 1-phenyl-2-heptyl-5-mercapto-1,3,4-triazole and 5 kg of a 20 weight % aqueous solution of denatured polyvinyl alcohol (Poval MP203, manufactured by KURARAY CO., LTD.) were added with 8.3 kg of water, and mixed sufficiently to form a slurry. The slurry was fed by a diaphragm pump to a sand mill of horizontal type (UVM-2, manufactured by Imex Co.) containing zirconia beads having a mean diameter of 0.5 mm, and dispersed for 6 hours. Then, the slurry was added with water to adjust the concentration of the mercapto compound to 10 weight % to obtain a mercapto compound dispersion. The mercapto compound particles contained in the mercapto compound dispersion obtained as described above had a median diameter of 0.40 $\mu$m and the maximum particle size of 2.0 $\mu$m or less. The mercapto compound dispersion was filtered through a polypropylene filter having a pore size of 10.0 $\mu$m to remove dusts and so forth, and stored. The dispersion was filtered through a polypropylene filter having a pore size of 10.0 $\mu$m immediately before use.

(Preparation of 20 Weight Dispersion of Organic Polyhalogenated Compound 1)

5 kg of tribromomethylnaphthylsulfone, 2.5 kg of a 20 weight % aqueous solution of denatured polyvinyl alcohol (Poval MP203, manufactured by KURARAY CO., LTD.) and 213 g of 20 weight % aqueous solution of sodium triisopropylnaphthalenesulfonate were added with 10 kg of water, and mixed sufficiently to form slurry. The slurry was fed by a diaphragm pump to a sand mill of horizontal type (UVM-2, manufactured by Imex Co.) containing zirconia beads having a mean diameter of 0.5 mm, and dispersed for 5 hours. Then, the slurry was added with 0.2 g of benzisothiazolinrone sodium salt and water to adjust the concentration of the organic polyhalogenated compound to 20 weight % to obtain an organic polyhalogenated compound! dispersion. The organic polyhalogenated compound particles contained in the polyhalogenated compound dispersion obtained as described above had a median diameter of 0.36 $\mu$m and the maximum particle size of 2.0 $\mu$m or less. The obtained organic polyhalogenated compound dispersion was filtered through a polypropylene filter having a pore size of 3.0 $\mu$m to remove dusts and so forth, and stored.

(Preparation of 25 Weight % Dispersion of Organic Polyhalogenated Compound 2)

A dispersion was prepared in the same manner as the preparation of the 20 weight % dispersion of organic polyhalogenated compound 1 except that 5 kg of tribromomethyl (4-(2,4,6-trimethylphenylsulfonyl)phenyl)sulfone was used instead of 5 kg of tribromomethylnaphthylsulfone, diluted to adjust the concentration of the organic polyhalogenated compound to 25 weight %, and then filtered. The organic polyhalogenated compound particles contained in the organic polyhalogenated compound dispersion obtained as described above had a median diameter of 0.38 $\mu$m and the maximum particle size of 2.0 $\mu$m or less. The obtained organic polyhalogenated compound dispersion was filtered through a polypropylene filter having a pore size of 3.0 $\mu$m to remove insoluble solids such as dusts, and then stored.

(Preparation of 30 Weight % Dispersion of Organic Polyhalogenated Compound 3)

A dispersion was prepared in the same manner as the preparation of the 20 weight % dispersion of organic polyhalogenated compound 1 except that 5 kg of tribromomethylphenylsulfone was used instead of 5 kg of tribromomethylnaphthylsulfone and the amount of the 20 weight % aqueous solution of MP203 was changed to 5 kg, diluted to adjust the concentration of the organic polyhalogenated compound to 30 weight %, and then filtered. The organic polyhalogenated compound particles contained in the organic polyhalogenated compound dispersion obtained as described above had a median diameter of 0.41 $\mu$m and the maximum particle size of 2.0 $\mu$m or less. The obtained organic polyhalogenated compound dispersion was filtered through a polypropylene filter having a pore size of 3.0 $\mu$m to remove dusts and so forth, and stored.

(Preparation of 5 Weight % Solution of Phthalazine Compound)

8 kg of denatured polyvinyl alcohol (Poval MP-203, manufactured by KURARAY CO., LTD.) was dissolved in 174.57 kg of water and then added with 3.15 kg of 20 weight % aqueous solution of sodium triisopropylnaphthalenesulfonate and 14.28 kg of 70 weight % aqueous solution of 6-isopropylphthalazine to obtain a 5 weight % solution of 6-isopropylphthalazine.

(Preparation of 20 Weight % Dispersion of Pigment)

64 g of C.I. Pigment Blue 60 and 6.4 g of Demor N manufactured by Kao Corporation were added with 250 g of water and mixed sufficiently to provide slurry. Then, 800 g of zirconia beads having a mean diameter of 0.5 mm were placed in a vessel together with the slurry, and the slurry was dispersed by a dispersing machine (¼ G Sand Grinder Mill; manufactured by Imex Co.) for 25 hours to obtain a pigment dispersion. The pigment particles contained in the pigment dispersion obtained as described above had a mean particle size of 0.21 $\mu$m.

(Preparation of 40 Weight % SBR Latex)

SBR latex purified by ultrafiltration (UF) was obtained as follows.

The SBR latex mentioned, below diluted by 10 times with distilled water was diluted and purified by using an UF-purification module FS03-FC-FUYO3A1 (manufactured by Daisen Membrane System K.K.) until the ion conductivity became 1.5 mS/cm, and added with Sandet-BL (manufactured by SANYO CHEMICAL INDUSTRIES, LTD.) to a concentration of 0.22% by weight. Further, the latex was added with NaOH and $NH_4OH$ to adjust the ratio $Na^+$ ion:$NH_4^+$ ion to 1:2.3 (molar ratio) and pH to 8.4. At this point, the concentration of the latex was 40% by weight [SBR latex: a latex of -St(68)-Bu(29)-AA(3)-].

The latex had the following characteristics: mean particle size of 0.1 $\mu$m, concentration of 45%, equilibrium moisture content at 25° C., relative humidity 60% of 0.6% by weight, and ion conductivity of 4.2 mS/cm (measured for the latex stock solution (40%) at 25° C. by using a conductometer, CM-30S, manufactured by Toa Electronics, Ltd.).

(Preparation of Coating Solution for Emulsion Layer (Image-forming Layer))

1.1 g of the 20 weight % aqueous dispersion of the pigment obtained above, 103 g of the organic acid silver saltdispersion, 5 g of the 20 weight % aqueous solution of polyvinyl alcohol, PVA-205 (manufactured by KURARAY CO. LTD.), 25 g of the 25 weight % reducing agent dispersion, 16.3 g in total of Organic polyhalogenated compound dispersions 1, 2 and 3 (weight ratio=5:1:3), 6.2 g of the 10% mercapto compound dispersion, 106 g of the 40 weight % SBR latex purified by ultrafiltration (UF) and undergone pH adjustment, and 18 ml of the 5 weight % solution of the phthalazine compound were combined, added with 10 g of Mixed silver halide emulsion 1-A, and mixed sufficiently to prepare a coating solution for an emulsion layer. The coating solution as obtained was fed to a coating die in such a feeding amount giving a coating amount of 70 ml/m$^2$ and coated.

(Preparation of Coating Solution for Emulsion Surface Protection and Stress Prevention Layer)

772 g of a 10 weight % aqueous solution of polyvinyl alcohol, PVA-205 (manufactured by KURARAY CO., LTD.), 5.3 g of the 20 weight % dispersion of the pigment, and 226 g of a 27.5 weight % latex of methyl methacrylate/styrene/butyl acrylate/hydroxyethyl methacrylate/acrylic acid copolymer (copolymerization ratio (by weight): 64/9/20/5/2) were added with 2 ml of a 5 weight % aqueous solution of Aerosol OT (manufactured by American Cyanamid Company), 10.5 ml of a 20 weight % aqueous solution of phthalic acid diammonium salt and water in such an amount that gave a total amount of 880 g to form a coating solution for protection and stress prevention layer. This coating solution was fed to a coating die in such an amount that gave a coating amount of 10 ml/m$^2$.

The viscosity of the coating,solution measured by a B-type viscometer at 40° C. (Rotor No. 1, 60 rpm) was 21 [mPa·s].

(Preparation of Coating Solution for 1st Protective Layer on Emulsion Layer Surface)

64 g of inert gelatin was dissolved in water, added with 80 g of a 27.5 weight % latex solution of methyl methacrylate/styrene/butyl acrylate/hydroxyethyl methacrylate/acrylic acid copolymer (copolymerization ratio (by weight): 64/9/20/5/2), 23 ml of a 10 weight % methanol solution of phthalic acid, 23 ml of a 10 weight % aqueous solution of 4-methylphthalic acid, 28 ml of 1 N sulfuric acid, 5 ml of a 5 weight % aqueous solution of Aerosol OT (manufactured by American Cyanamid Company), 0.5 g of phenoxyethanol, 0.1 g of benzoisothiazolinone, and water in such an amount that gave a total amount of 750 g to form a coating solution. The coating solution was mixed with 26 ml of 4 weight % chromium alum by a static mixer immediately before coating, and fed to a coating die in such an amount that gave a coating amount of 18.6 ml/m$^2$.

The viscosity of the coating solution measured by a B-type viscometer (Rotor No. 1, 60 rpm) at 40° C. was 17 [mPa·s].

(Preparation of Coating Solution for 2nd Protective Layer on Emulsion Layer Surface)

80 g of inert gelatin was dissolved in water, added with 102 g of a 27.5 weight % latex solution of methyl methacrylate/styrene/butyl acrylate/hydroxyethyl methacrylate/acrylic acid copolymer (copolymerization ratio (by weight): 64/9/20/5/2), 3.2 ml of a 5 weight % solution of N-perfluorooctylsulfonyl-N-propylalanine potassium salt, 32 ml of a 2 weight % aqueous solution of polyethylene glycol mono(N-perfluorooctylsulfonyl-N-propyl-2-aminoethyl) ether [average polymerization degree of ethylene oxide=15], 23; ml of a 5 weight % aqueous solution of Aerosol TO (manufactured by American Cyanamid Company), 4 g of polymethyl methacrylate microparticles (mean particle size: 0.7 μm), 21 g of polymethyl methacrylate microparticles (mean particle size: 6.4 μm), 1.6 g of 4-methylphthalic acid, 4.8 g of phthalic acid, 44 ml of 1 N sulfuric acid, 10 mg of benzoisothiazolinone and water in such an amount that gave a total amount of 650 g. The mixture was further mixed with 445 ml of an aqueous solution containing 4 weight % chromium alum and 0.67 weight % of phthalic acid by a static mixer immediately before coating to form a coating solution for surface protective layer, which was fed to a coating die in such an amount that gave a coating amount of 8.3 ml/m$^2$.

The viscosity of the coating solution measured by a B-type viscometer (Rotor No. 1, 60 rpm) at 40° C. was 9 [mPa·s].

(Preparation of Photothermographic Material)

On the back side of the aforementioned support having an undercoat layer, the coating solution for antihalation layer and the coating solution for back surface protective layer were simultaneously applied as stacked layers to adjust the applied solid content amount of the solid microparticle dye in the antihalation layer to 0.04 g/m$^2$, and the applied amount of gelatin in the protective layer to 1.7 g/m$^2$, and dried to form an antihalation back layer., Then, on the side opposite to the back side, an emulsion layer (coated silver amount of the silver halide was 0.14 g/m$^2$), protection and stress prevention layer, first protective layer, and second protective layer were simultaneously applied in this order from the undercoat layer by the slide bead application method as stacked layers to form a sample of photothermographic material.

The coating was performed at a speed of 160 m/min. The gap between the tip of coating die and the support was set to be 0.14 to 0.28 mm, and the coated width was controlled so that it spread by each 0.5 mm at both sides relative to the projecting slit width of the coating solution. The pressure in the reduced pressure chamber was adjusted to be lower than the atmospheric pressure by 392 Pa. In this process, handling, temperature and humidity were controlled so as not to cause electrostatical charge of the support, and electrostatic charge was further eliminated by ionized wind immediately before the coating. In the subsequent chilling zone, the material was blown with air having a dry-bulb temperature of 18° C. and a wet-bulb temperature of 12° C. for 30 seconds to cool the coating solutions. Then, in the floating type drying zone in a coiled shape, the material was blown with drying air showing a dry-bulb temperature of 30° C. and a wet-bulb temperature of 18° C. for 200 seconds. Subsequently, the material was passed through a drying zone of 70° C. for 20 seconds, and then another drying zone of 90° C. for 10 seconds, and cooled to 25° C. to evaporate the solvent in the coating solution. The average wind velocities of the wind applied to the coated layer surface in the chilling zone and the drying zones were 7 m/sec.

The prepared photothermographic material had matting degrees of 55 seconds for the image-forming layer side, and 130 seconds for the back surface, in terms of Beck's smoothness.

Spectral sensitizing dye A

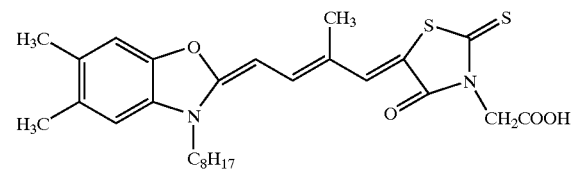

Tellurium sensitizer B

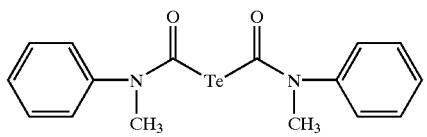

Base precursor compound 11

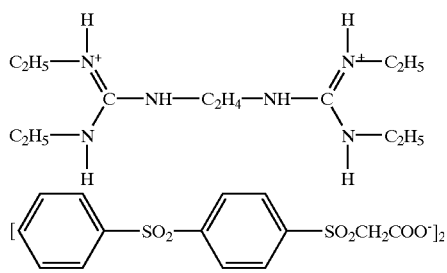

Cyanine dye compound 13

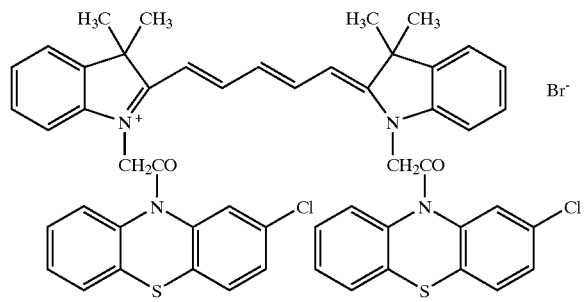

Blue dye compound 14

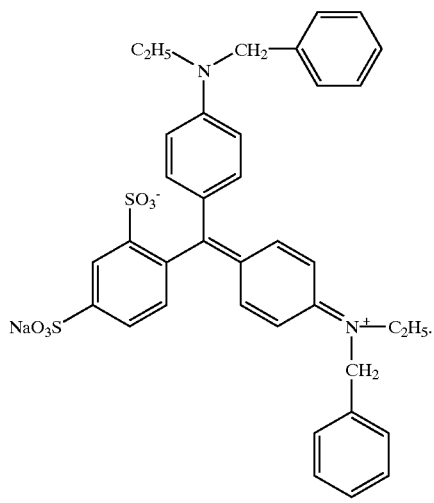

(Evaluation of Photographic Performance)

Each photothermographic material was light-exposed and heat-developed (at about 120° C.) by using Fuji Medical Dry Laser Imager FM-DP L (equipped with a semiconductor laser of 660 nm and a maximum output of 60 mW (IIIB)), and the obtained image was evaluated by a densitometer. The performance was evaluated in terms of Dmin, Dmax and sensitivity as the measurement results, which are shown in Table 1. The sensitivity was evaluated as a reciprocal of a ratio of exposure amounts giving a density higher than Dmin by 1.0, and shown in Table 1 as a relative value based on the sensitivity obtained for Sample No. 1, which was defined as 100.

It can be seen that Sample Nos. 3 to 5 according to the present invention had Dmin, Dmax and sensitivity superior to those of the comparative samples.

TABLE 1

| Sample No. | Aliphatic acid silver salt dispersion No. | Dmin | Dmax | Relative sensitivity | Note |
|---|---|---|---|---|---|
| 1 | 1 | 0.20 | 3.50 | 100 | Comparative |
| 2 | 2 | 0.25 | 2.68 | 48 | Comparative |
| 3 | 1-A | 0.18 | 3.75 | 125 | Present Invention |
| 4 | 1-B | 0.16 | 3.68 | 105 | Present Invention |
| 5 | 1-C | 0.17 | 3.77 | 110 | Present Invention |

Example 2

(Preparation of Comparative Organic Acid Silver Salt 3)

87.6 kg of behenic acid (Edenor C22-85R, trade name, manufactured by Henkel Co.), 423 L of distilled water, 49.2 L of a 5 N aqueous solution of NaOH, and 120 L of tert-butanol were mixed and reacted with stirring at 75° C. for one hour to obtain a solution of sodium behenate. Separately, 206.2 L of an aqueous solution containing 40.4 kg of silver nitrate (pH 4.0) was prepared and kept at 10° C. A mixture of 635 L of distilled water and 30 L of tert-butanol contained in a reaction vessel kept at 30° C. was added with the whole amount of the aforementioned sodium behenate solution, and with the whole amount of the aqueous silver nitrate solution at constant flow rates over the periods of 62 minutes and 10 seconds, and 60 minutes, respectively. In this procedure, the solutions were added in such a manner that only the aqueous silver nitrate solution was added for 7 minutes and 20 seconds after start of the addition of the aqueous silver nitrate solution, and for 9 minutes and 30 seconds after completion of the addition of the aqueous silver nitrate solution, only the sodium behenate solution was added. In this operation, the outside temperature was controlled to adjust the temperature in the reaction vessel to 30° C. and keep the liquid temperature constant. The piping of the addition system for the sodium behenate solution was heated by steam trace, and the steam opening was controlled to adjust the liquid temperature at the outlet orifice of the addition nozzle to 75° C. The piping of the addition system for the aqueous silver nitrate solution was kept cooled by circulating cold water outside a double pipe. The addition position of the sodium behenate solution and the addition position of the aqueous silver nitrate solution were arranged symmetrically relative to the stirring axis at the center, and the positions are controlled at heights so as not to contact with the reaction mixture.

After completion of the addition of the sodium behenate solution, the mixture was added with 88 kg of 10 weight % aqueous solution of polyvinyl alcohol (PVA-217, trade name, average polymerization number: about 1700) and left with stirring for 20 minutes at the same temperature, and then the temperature was decreased to 25° C.

The subsequent desalting operation and so forth were performed in the same manner as the preparation of the comparative Organic acid silver salt dispersion 2 in Example 1. When the shape of the obtained silver behenate grains was evaluated by an electron microscopic photography, the grains were scaly crystals having a mean diameter as spheres of 0.50 μm, and a variation coefficient of 14% for mean diameter as spheres.

(Preparation of Inventive Organic Acid Silver Salt Dispersion 2-D)

87.6 kg of behenic acid (Edenor C22-85R, trade name, manufactured by Henkel Co.), 423 L of distilled water, 49.2 L of a 5 N aqueous solution of NaOH, and 120 L of tert-butanol were mixed and allowed to react with stirring at 75° C. for one hour to obtain a solution of sodium behenate. Separately, 206.2 L of an aqueous solution containing 40.4 kg of silver nitrate (pH 4.0) was prepared and kept at 10° C. A mixture of 600 L of distilled water, 30 L of tert-butanol and 35 kg of a 10 weight % of aqueous solution of triisopropylnaphthalenesulfonic acid (molecular weight: 357) contained in a reaction vessel kept at 30° C. was added with the whole amount of the aforementioned sodium behenate solution, and with the whole amount of the aqueous silver nitrate solution at constant flow rates over the periods of 62 minutes and 10 seconds, and 60 minutes, respectively. In this procedure, the solutions were added in such a manner that only the aqueous silver nitrate solution was added for 7 minutes and 20 seconds after start of the addition of the aqueous silver nitrate solution, and for 9 minutes and 30 seconds after completion of the addition of the aqueous silver nitrate solution, only the sodium behenate solution was added. In this operation, the outside temperature was controlled to adjust the temperature in the reaction vessel to 30° C. and keep the liquid temperature constant. The piping of the addition system for the sodium behenate solution was heated by steam trace and the steam opening was controlled to adjust the liquid temperature at the outlet orifice of the addition nozzle to 75° C. The piping of the addition system for the aqueous silver nitrate solution was kept cooled by circulating cold water outside a double pipe. The addition position of the sodium behenate solution and the addition position of the aqueous silver nitrate solution were arranged symmetrically relative to the stirring axis at the center, and the positions are controlled at heights not to contact with the reaction mixture.

After completion of the addition of the sodium behenate solution, the mixture was added with 88 kg of 10 weight % aqueous solution of polyvinyl alcohol (PVA-217, trade name, average polymerization degree: about 1700) and left with stirring for 20 minutes at the same temperature, and then the temperature was decreased to 25° C. When the shape of the obtained silver behenate grains was evaluated by an electron microscopic photography, the grains were scaly crystals having a mean diameter as spheres of 0.51 µm, and a variation coefficient of 12% for mean diameter as spheres.

The subsequent desalting operation and so forth were performed in the same manner as the preparation of the comparative Organic acid silver salt dispersion 2 in Example 1.

Coated Samples Nos. 6 and 7 for evaluation were prepared in the same manner as in Example 1 by using the obtained organic acid silver salt dispersions, and treated and evaluated in the same manner as Example 1. The results are summarized in Table 2. It can be seen that Sample No. 7 according to the present invention had superior Dmin, Dmax and sensitivity.

TABLE 2

| Sample No. | Aliphatic acid silver salt dispersion No. | Dmin | Dmax | Relative sensitivity | Note |
|---|---|---|---|---|---|
| 1 | 1 | 0.20 | 3.50 | 100 | Comparative |
| 6 | 3 | 0.30 | 2.56 | 39 | Comparative |
| 7 | 2-D | 0.15 | 3.72 | 110 | Present Invention |

Example 3
(Preparation of PET Support)

Using terephthalic acid and ethylene glycol, PET having an intrinsic viscosity IV of 0.66 (measured in phenol/tetrachloroethane=6/4 (weight ratio) at 25° C.) was obtained in a conventional manner. The PET was pelletized, and the pellets were dried at 130° C. for 4 hours, melted at 300° C., extruded from a T-die, and quenched to prepare an unstretched film having a thickness of 175 µm after thermal fixation.

The film was stretched along the longitudinal direction by 3.3 times using rollers having different peripheral speeds and then stretched along the transverse direction by 4.5 times using a tenter In this process, the temperatures were 110° C. and 130° C., respectively. The film was then subjected to thermal fixation at 240° C. for 20 seconds and relaxed by 4% along the transverse direction at the same temperature. Then, after chucks of the tenter were released, the both edges of the film were knurled, and the film was rolled up at 4 kg/cm² to provide a roll of the film having a thickness of 175 µm.

(Surface Corona Discharging Treatment)

Using a solid state corona discharging treatment machine Model 6KVA manufactured by Piller Inc., both surfaces of the support were treated at room temperature at 20 m/minute. From the read out values of the electric current and voltage, it was seen that the treatment of 0.375 kV·A·minute/m² was applied to the support in this procedure. The treated frequency in this operation was 9.6 kHz and the gap clearance between the electrode and the dielectric roll was 1.6 mm.

(Preparation of Undercoated Support)

(1) Preparation of coating solution for undercoat layer

| | |
|---|---|
| Formulation (1) (for undercoat layer on photosensitive layer side) | |
| Pesresin A-515GB made by Takamatsu Yushi K. K. (30 weight % solution) | 234 g |
| Polyethylene glycol monononylphenyl ether (mean ethylene oxide number = 8.5, 10 weight % solution) | 21.5 g |
| MP-1000 made by Soken Kagaku K. K. (polymer microparticles, mean particle size: 0.4 µm) | 0.91 g |
| Distilled water | 744 ml |
| Formulation (2) (for 1st layer on back surface) | |
| Butadiene-styrene copolymer latex (solid content: 40% by weight, weight ratio of butadiene/styrene = 32/68) | 158 g |
| 2,4-Dichloro-6-hydroxy-S-triazine sodium salt (8 weight % aqueous solution) | 20 g |
| 1 weight % Aqueous solution of sodium laurylbenzenesulfonate | 10 ml |
| Distilled water | 854 ml |
| Formulation (3) (for 2nd layer on back surface side) | |
| $SnO_2$/SbO (weight ratio: 9/1, mean particle size: 0.038 µm, 17 weight % dispersion) | 84 g |
| Gelatin (10% aqueous solution) | 89.2 g |
| Metorose TC-5 made by Shin-Etsu Chemical Co., Ltd. (2% aqueous solution) | 8.6 g |
| MP-1000 (polymer microparticles) made by Soken Kagaku K. K. | 0.01 g |
| 1 weight % Aqueous solution of sodium dodecylbenzenesulfonate | 10 ml |
| NaOH (1%) | 6 ml |
| Proxel (made by ICI Co.) | 1 ml |
| Distilled water | 805 ml |

(Preparation of Undercoated Support)

After applying the aforementioned corona discharging treatment to both surfaces of the aforementioned biaxially stretched polyethylene terephthalate support having a thickness of 175 μm, one surface (photosensitive layer coating surface side) thereof was coated with the undercoating solution of Formulation (1) by a wire bar in a wet coating amount of 6.6 ml/m$^2$ (per one surface) and dried at 180° C. for 5 minutes. Then, the back surface thereof was coated with the undercoating solution of Formulation (2) by a wire bar in a wet coating amount of 5.7 ml/m$^2$ and dried at 180° C. for 5 minutes. Further, the back surface thus coated was coated with the undercoating solution of Formulation (3) by a wire bar in a wet coating amount of 7.7 ml/m$^2$ and dried at 180° C. for 6 minutes to prepare an undercoated support.

(Preparation of Coating Solution for Back Surface)
(Preparation of Solid Microparticle Dispersion (a) of Base Precursor)

64 g of Base precursor compound 11, 28 g of diphenylsulfone and 10 g of a surface active agent, Demor N (manufactured by Kao Corporation), were mixed with 220 ml of distilled water, and the mixture was beads—dispersed using a sand mill (¼ Gallon Sand Grinder Mill, manufactured by Imex Co.) to obtain Solid microparticle dispersion (a) of the base precursor compound having a mean particle size of 0.2 μm.

(Preparation of Dye Solid Microparticle Dispersion)

9.6 g of Cyanine dye compound 13 and 5.8 g of sodium p-dodecylbenzenesulfonate were mixed with 305 ml of distilled water and the mixture was beads—dispersed using a sand mill (¼ Gallon Sand Grinder Mill, manufactured by Imex Co.) to obtain a dye solid microparticle dispersion having a mean particle size of 0.2 μm.

(Preparation of Coating Solution for Antihalation Layer)

17 g of gelatin, 9.6 g of polyacrylamide, 70 g of the aforementioned Solid microparticle dispersion (a) of the base precursor, 56 g of the aforementioned dye solid microparticle dispersion, 1.5 g of polymethyl methacrylate microparticles (mean particle size 6.5 μm), 0.03 g of benzoisothiazolinone, 2.2 g of sodium polyethylenesulfonate, 0.2 g of Blue dye compound 14 and 844 ml of water were mixed to prepare a coating solution for antihalation layer.

(Preparation of Coating Solution for Back Surface Protective Layer)

In a container kept at 40° C., 50 g of gelatin, 0.2 g of sodium polystyrenesulfonate, 2.4 g of N,N-ethylenebis (vinylsulfonacetamide), 1 g of sodium t-octylphenoxyethoxyethanesulfonate, 30 mg of benzoisothiazolinone, 37 mg of N-perfluorooctylsulfonyl-N-propylalanine potassium salt, 0.15 g of polyethyleneglycol mono-(N-perfluorooctylsulfonyl-N-propyl-2-aminoethyl) ether [average polymerization degree of ethylene oxide: 15], 32 mg of $C_8F_{17}SO_3K$, 64 mg of $C_8F_{17}SO_2N(C_3H_7)$—$(CH_2CH_2O)_4(CH_2)_4$—$SO_3Na$, 8.8 g of an acrylic acid/ethyl acrylate copolymer (copolymerization ratio (by weight): 5/95), 0.6 g of Aerosol OT (manufactured by American Cyanamid Company), 1.8 g (as liquid paraffin) of a liquid paraffin emulsion and 950 ml of water were mixed to form a coating solution for a back surface protective layer.

(Preparation of Silver Halide Emulsion 1)

1421 ml of distilled water was added with 8.0 ml of a 1% by weight potassium bromide solution, and further added with 8.2 ml of 1 N nitric acid and 20 g of phthalized gelatin. Separately, Solution A was prepared by adding distilled water to 37.04 g of silver nitrate to dilute the agent to 159 ml, and Solution B was prepared by diluting 32.6 g of potassium bromide with distilled water to a volume of 200 ml. To the aforementioned mixture maintained at 37° C. and stirred in a titanium-coated stainless steel reaction vessel, the whole volume of Solution A was added by the control double jet method over 1 minute at a constant flow rate while pAg was maintained at 8.1. Solution B was also added by the control double jet method. Then, the mixture was added with 30 ml of 3.5 weight % aqueous hydrogen peroxide solution, and further added with 36 ml of a 3 weight % aqueous solution of benzimidazole. Separately, Solution A2 was prepared by diluting Solution A with distilled water to a volume of 317.5 ml, and Solution B2 was prepared by dissolving tripotassium hexachloroiridate in Solution B in such an amount that its final concentration became $1 \times 10^{-4}$ mole per mole of silver, and diluting the obtained solution with distilled water to a volume twice as much as the volume of Solution B, 400 ml. The whole volume of Solution A2 was added to the mixture again by the control double jet method over 10 minutes at a constant flow rate while pAg was maintained at 8.1. Solution B2 was also added by the control double jet method. Then, the mixture was added with 50 ml of a 0.5 weight % solution of 2-mercapto-5-methylbenzimidazole in methanol. After pAg was raised to 7.5 with silver nitrate, the mixture was adjusted to pH 3.8 using 1 N sulfuric acid, and the stirring was stopped. Then, the mixture was subjected to precipitation, desalting and washing with water, added with 3.5 g of deionized gelatin and 1 N sodium hydroxide to be adjusted to pH 6.0 and pAg of 8.2 to form a silver halide dispersion.

The grains in the resulting silver halide emulsion were pure silver bromide grains having a mean spherical diameter of 0.053 μm and a variation coefficient of 18% in terms of spherical diameter. The grain size and others were obtained from averages for 1000 grains by using an electron microscope. The [100] face ratio of these grains was determined to be 85% by the Kubelka-Munk method.

The aforementioned emulsion was added with 0.035 g of benzoisothiazolinone (added as a 3.5 weight % methanol solution of the compound) with stirring at 38° C., and after 40 minutes, added with the solid dispersion (an aqueous gelatin solution) of Spectral sensitizing dye A in an amount of $5 \times 10^{-3}$ mole per mole of silver. After 1 minutes, the mixture was warmed to 47° C., and after 20 minutes, added with $3 \times 10^{-5}$ mole of sodium benzenethiosulfonate per mole of silver. After 2 minutes, the mixture was added with Tellurium sensitizer B in an amount of $5 \times 10^{-5}$ mole per mole of silver followed by ripening for 90 minutes. Immediately before finishing the ripening, the mixture was added with 5 ml of a 0.5% by weight methanol solution of N,N'-dihydroxy-N"-diethylmelamine, and after lowering the temperature to 31° C., added with 5 ml of a 3.5 weight % methanol solution of phenoxyethanol, $7 \times 10^{-3}$ mole of 5-methyl-2-mercaptobenzimidazole per mole of silver, and $6.4 \times 10^{-3}$ mole of 1-phenyl-2-heptyl-5-mercapto-1,3,4-triazole per mole of silver to prepare Silver halide emulsion 1.

(Preparation of Silver Halide Emulsion 2)

In the same manner as the preparation of Silver halide emulsion 1 except that the liquid temperature upon forming the grains was changed from 37° C. to 50° C., a pure silver bromide cubic grain emulsion having a mean grain size of 0.08 μm as spheres and a variation coefficient of 15% for size as spheres was prepared. Further, as in the case of Silver halide emulsion 1, the steps of precipitation, desalting, washing with water and dispersion were performed. In the same manner as the preparation of Silver halide emulsion 1, except that the addition amount of Spectral sensitizing dye A was changed to $4.5 \times 10^{-3}$ mole per mole of silver, the spectral sensitization, the chemical sensitization, and the addition of 5-methyl-2-mercaptobenzimidazole and 1-phenyl-2-heptyl-5-mercapto-1,3,4-triazole were performed to obtain Silver halide emulsion 2.

(Preparation of Silver Halide Emulsion 3)

In the same manner as the preparation of Silver halide emulsion 1, except that the liquid temperature upon forming the grains was changed from 37° C. to 27° C., a pure silver bromide cubic grain emulsion having a mean grain size of 0.038 µm as spheres and a variation coefficient of 20% for size as spheres was prepared. As in the case of Silver halide emulsion 1, the steps of precipitation, desalting, washing with water and dispersion were performed. In the same manner as the preparation of Silver halide emulsion 1, except that the addition amount of Spectral sensitizing dye A was changed to $6 \times 10^{-3}$ mole per mole of silver, the spectral sensitization, the chemical sensitization, and the addition of 5-methyl-2-mercaptobenzimidazole and 1-phenyl-2-heptyl-5-mercapto-1,3,4-triazole were performed to obtain Silver halide emulsion 3.

(Preparation of Mixed Emulsion A for Coating Solution)

70% by weight of Silver halide emulsion 1, 15% by weight of Silver halide emulsion 2 and 15% by weight of Silver halide emulsion 3 were mixed and added with benzothiazolium iodide in an amount of $7 \times 10^{-3}$ mole per mole of silver as a 1% by weight aqueous solution to form Mixed emulsion A for coating solution.

(Preparation of Comparative Organic Acid Silver Salt 3-A)

87.6 kg of behenic acid (Edenor C22-85R, trade name, manufactured by Henkel Co.), 423 L of distilled water, 49.2 L of a 5 N aqueous solution of NaOH, and 120 L of tert-butanol were mixed and reacted with stirring at 75° C. for one hour to obtain a solution of sodium behenate. Separately, 206.2 L of an aqueous solution containing 40.4 kg of silver nitrate (pH 4.0) was prepared and kept at 10° C. A mixture of 635 L of distilled water and 30 L of tert-butanol contained in a reaction vessel kept at 30° C. was added with the whole amount of the aforementioned sodium behenate solution, and with the whole amount of the aqueous silver nitrate solution at constant flow rates over the periods of 93 minutes and 90 minutes, respectively. In this procedure, the solutions were added in such a manner that only the aqueous silver nitrate solution was added for 11 minutes after starting the addition of the aqueous silver nitrate solution, and for 14 minutes after finishing the addition of the aqueous silver nitrate solution, only; the sodium behenate solution was added. In this operation, the outside temperature was controlled to adjust the temperature in the reaction vessel to 30° C. and keep the liquid temperature constant. The piping of the addition system for the sodium behenate solution was temperature-controlled by a double pipe, and cooled water was circulated in a jacket at the outer part of the double pipe to adjust the liquid temperature at the outlet orifice of the addition nozzle to 10° C. The addition position of the sodium behenate solution and the addition position of the aqueous silver nitrate solution were arranged symmetrically relative to the stirring axis as the center, and the positions are controlled at heights not to contact with the reaction mixture.

After completion of the addition of the sodium behenate solution, the mixture was left with stirring for 20 minutes at the same temperature and then the temperature was lowered to 25° C. The solid content was then recovered by a suction filtration and the solid content was washed with water until electric conductivity of the filtrate became 50 µS/cm. Thus, an organic acid silver salt was obtained. The obtained solid content was stored as a wet cake without being dried.

To the wet cake corresponding to 100 g of the dry solid content was added with 7.4 g of polyvinyl alcohol (PVA-217, trade name) and water to make the total amount 385 g, and the mixture was pre-dispersed by a homomixer.

Then, the pre-dispersed stock dispersion was treated three times by using a dispersing machine (Microfluidizer-M-110S-EH; trade name, manufactured by Microfluidex International Corporation, using G10Z interaction chamber) with a pressure controlled to be 1750 kg/cm² to obtain a silver behenate dispersion. During the cooling operation, a dispersion temperature of 18° C. was achieved by providing coiled heat exchangers fixed before and after the interaction chamber and controlling the temperature of the refrigerant.

When the shape of the obtained silver behenate grains was evaluated by an electron microscopic photography, the grains were scaly crystals having a=0.14 µm, b=0.4 µm, and c=0.6 µm in mean values, a mean aspect ratio of 5.2, a mean diameter as spheres of 0.52 µm, and a variation coefficient of 15% for mean diameter as spheres (a, b and c have the meanings defined in the present specification).

(Preparation of Inventive Organic Acid Silver Salt Dispersion 3-B)

87.6 kg of behenic acid (Edenor C22-85R, trade name, manufactured by Henkel Co.), 423 L of distilled water, 49.2 L of a 5 N aqueous solution of NaOH, and 120 L of tert-butanol were mixed and reacted with stirring at 75° C. for one hour to obtain a solution of sodium behenate. Separately, 206.2 L of an aqueous solution containing 40.4 kg of silver nitrate (pH 4.0) was prepared and kept at 10° C. A surfactant solution prepared by adding Surfactant SI at a concentration of 45 mM/L to 635 L of distilled water and 30 L of tert-butanol and contained in a reaction vessel kept at 30° C. was added with the whole amount of the aforementioned sodium behenate solution, and with the whole amount of the aqueous silver nitrate solution at constant flow rates over the periods of 62 minutes and 10 seconds, and 60 minutes, respectively. In this procedure, the solutions were added in such a manner that only the aqueous silver nitrate solution was added for 7 minutes and 20 seconds after starting the addition of the aqueous silver nitrate solution. Then, the addition of the sodium behenate solution was started so that for 9 minutes and 30 seconds after finish of the addition of the aqueous silver nitrate solution, only the sodium behenate solution was added. In this operation, the outside temperature was controlled to adjust the temperature in the reaction vessel to 30° C. and keep the liquid temperature constant.

After completion of the addition of the sodium behenate solution, the temperature was decreased to 25° C. over 20 minutes, and the mixture was added with 108 L of 4 weight % solution of polyvinyl alcohol (PVA-217, trade name).

The obtained organic acid silver salt dispersion was subjected to desalting treatment by transferring the dispersion to an ultrafiltration apparatus shown in FIG. 1. The ultrafiltration apparatus was basically constituted by a tank 1 for stocking the organic acid silver salt dispersion, and a circulation pump 2 for feeding the stocked dispersion to an ultrafiltration module 3, and provided with a flowmeter 4 for measuring flow rate of supplemental pure water, a flowmeter 5 for measuring amount of permeated water, a pump 6 for washing in reverse direction, and so forth. The membrane module used was a hollow yarn type one, ACP-1050, produced by Asahi Chemical Industry Co., Ltd. The feeding flow rate was 18 L/minute, and the pressure difference before and after the module was 1.0 kg/cm².

The supplementation of pure water was stopped when the conductivity was decreased to 100 µS/cm, and the dispersion was concentrated to a concentration of 26% by weight. The solid concentration was measured by using a digital specific gravimeter Model DA-300, produced by Kyoto Denshi Co., Ltd., and the definitive content was determined from the absolute dry weight.

When the shape of the obtained silver behenate grains was evaluated by an electron microscopic photography, the grains were acicular crystals having a mean diameter as spheres of 0.27 µm, and a variation coefficient of 12% for mean diameter as spheres.

(Preparation of Inventive Organic Acid Silver Salt Dispersion 3-C)

Organic acid silver salt dispersion 3-C was prepared in exactly the same manner as that for Organic acid silver salt dispersion 3-B except that the surfactant as the aqueous solution added to a reaction vessel beforehand was changed to a 55 mM/L solution of Surfactant S2. When the grain shape of the obtained silver salt of organic acid was evaluated by an electron microscopic photography, the grains were acicular crystals having a mean diameter as spheres of 0.32 µm, and a variation coefficient of 12% for mean diameter as spheres.

(Preparation of Inventive Organic Acid Silver Salt Dispersion 3-D)

Organic acid silver salt dispersion 3-D was prepared in exactly the same manner as that for Organic acid silver salt dispersion 3-B except that the surfactant as the aqueous solution added to a reaction vessel beforehand was changed to a 65 mM/L solution of Surfactant S3. When the grain shape of the obtained silver salt of organic acid was evaluated by an electron microscopic photography, the grains were acicular crystals having a mean diameter as spheres of 0.39 µm, and a variation coefficient of 16% for mean diameter as spheres.

(Preparation of Inventive Organic Acid Silver Salt Dispersion 3-E)

Organic-acid silver salt dispersion 3-E was prepared in exactly the same manner as that for Organic acid silver salt dispersion 3-D except that Surfactant S3 (70 ml of 0.65 M/L aqueous solution) was added during the temperature decrease to 25° C. over 20 minutes after the completion of the addition of the silver behenate solution. When the grain shape of the obtained silver salt of organic acid was evaluated by an electron microscopic photography, the grains were scaly crystals having a mean diameter as spheres of 0.47 µm, and a variation coefficient of 22% for mean diameter as spheres.

(Preparation of Inventive Organic Acid Silver Salt Dispersion 3-F)

Organic acid silver salt dispersion 3-F was prepared in exactly the same manner as that for Organic acid silver salt dispersion 3-B except that the surfactant as the aqueous solution added to a reaction vessel beforehand was changed to a 65 mM/L solution of Surfactant S4. When the grain shape of the obtained silver salt of organic acid was evaluated by an electron microscopic photography, the grains were tabular crystals having a mean diameter as spheres of 0.34 µm, and a variation coefficient of 14% for mean diameter as spheres.

(Preparation of Comparative Organic Acid Silver Salt Dispersion 3-G)

Organic acid silver salt dispersion 3-G was prepared in exactly the same manner as that for Organic acid silver salt dispersion 3-B except that the surfactant as the aqueous solution added to a reaction vessel beforehand was changed to a 0.5 mM/L solution of polyvinyl alcohol (PVA-217, trade name). When the grain shape of the obtained silver salt of organic acid was evaluated by an electron microscopic photography, the grains were scaly crystals having a mean diameter as spheres of 0.47 µm with remarkable aggregation.

(Preparation of Comparative Organic Acid Silver Salt Dispersion 3-H)

Organic acid silver salt dispersion 3-H was prepared in exactly the same manner as that for Organic acid silver salt dispersion 3-B except that the surfactant as the aqueous solution added to a reaction vessel beforehand was changed to a 0.5 mM/L solution of Surfactant S5. When the grain shape of the obtained silver salt of organic acid was evaluated by an electron microscopic photography, the grains were scaly crystals having a mean diameter as spheres of 0.15 µm with remarkable aggregation.

(Preparation of Comparative Organic Acid Silver Salt Dispersion 3-I)

Organic acid silver salt dispersion 3-I was prepared in exactly the same manner as that for Organic acid silver salt dispersion 3-B except that the surfactant as the aqueous solution added to a reaction vessel beforehand was changed to a 0.5 mM/L solution of Surfactant S6. When the grain shape of the obtained silver salt of organic acid was evaluated by an electron microscopic photography, the grains were scaly crystals having a mean diameter as spheres of 0.25 µm with remarkable aggregation.

(Preparation of Inventive Organic Acid Silver Salt 3-J)

An organic acid silver salt stock dispersion was prepared in the same manner as that for Organic acid silver salt dispersion 3-E except that the surfactant was changed to Surfactant S4 (70 ml of 0.56 M/L solution) and polyvinyl alcohol was not added.

The obtained organic acid silver salt stock dispersion was transferred to the ultrafiltration apparatus shown in FIG. 1 and subjected to the desalting treatment in the same manner as that for Organic acid silver salt dispersion 3-B. However, the liquid supplemented in the constant: volume dilution was changed from pure water to a 45 mM/L solution of Surfactant S1, and 108 ml of 4 weight % solution of polyvinyl alcohol (PVA-217, trade name) was added when the conductivity became lower than 2,000 µS/cm. Further, after 5-fold constant volume dilution was performed by supplementing pure water, the supplementation of pure water was stopped, and the dispersion was concentrated to 26 weight % concentration.

When the shape of the obtained silver behenate grains was evaluated by an electron microscopic photography, the grains were tabular crystals having a mean diameter as spheres of 0.34 µm, a, nd a variation coefficient of 18% for mean diameter as spheres.

(Preparation of Inventive Organic Acid Silver Salt Dispersion 3-K)

Organic acid silver salt dispersion 3-K was prepared in exactly the same manner as that for Organic acid silver salt dispersion 3-E except that the low molecular weight surfactant was changed from Surfactant S3 to S7 and the macromolecular dispersing agent is changed from the polyvinyl alcohol to polyvinylpyrrolidone (PVP K-30, trade name, produced by GAF Corporation). When the grain shape of the obtained silver salt of organic acid was evaluated by an electron microscopic photography, the grains were scaly crystals having a mean diameter as spheres of 0.63 µm, and a variation coefficient of 19% for mean diameter as spheres.

(Preparation of Inventive Organic Acid Silver Salt Dispersion 3-L)

Organic acid silver salt dispersion 3-L was prepared in exactly the same manner as that for Organic acid silver salt dispersion 3-K except that the macromolecular dispersing agent is changed from the polyvinylpyrrolidone to hydroxyethylcellulose (SP550, trade name, produced by Daicel Chemical Industries, Ltd.). When the grain shape of the obtained silver salt of organic acid was evaluated by an electron microscopic photography, the grains were scaly crystals having a mean diameter as spheres of 0.59 μm, and a variation coefficient of 21% for mean diameter as spheres.
(Preparation of Comparative Organic Acid Silver Salt 3-M)

An organic acid silver salt stock dispersion was prepared in the same manner as that for Organic acid silver salt dispersion 3-B except that the polyvinyl alcohol was not added.

The obtained organic acid silver salt stock dispersion was transferred to the ultrafiltration apparatus shown in FIG. 1 and subjected to the desalting treatment in the same manner as that for Organic acid silver salt dispersion 3-B. However, the liquid supplemented in the constant volume dilution was changed from pure water to a 45 mM/L solution of Surfactant S1, and the supplementation of the solution of Surfactant Si was stopped when the conductivity decreased to 500μS/cm, and the dispersion was concentrated to a concentration of 26% by weight. When the shape of the obtained silver behenate grains was evaluated by an electron microscopic photography, the grains were acicular crystals having a mean diameter as spheres of 0.27 9 μm, and a variation coefficient of 27% for mean diameter as spheres.

(Preparation of Comparative Organic Acid Silver Salt Dispersion 3-N)

Organic acid silver salt dispersion 3-N was prepared in exactly the same manner as that for Organic acid silver salt dispersion 3-M except that the surfactant as the aqueous solution added to a reaction vessel beforehand was changed to a 55 mM/L solution of Surfactant S2. When the grain shape of the obtained silver salt of organic acid was evaluated by an electron microscopic photography, the grains were acicular crystals having a mean diameter as spheres of 0.31 μm, and a variation coefficient of 17% for mean diameter as spheres.

(Preparation of Comparative Organic Acid Silver Salt Dispersion 3-O)

Organic acid silver salt dispersion 3-O was prepared in exactly the same manner as that for Organic acid silver salt dispersion 3-M except that the surfactant as the aqueous solution added to a reaction vessel beforehand was changed to a 65 mM/L solution of Surfactant S3. When the grain shape of the obtained silver salt of organic acid was evaluated by an electron microscopic photography, the grains were acicular crystals having a mean diameter as spheres of 0.40 μm, and a variation coefficient of 14% for mean diameter as spheres.

Surfactant S1
Sodium dioctyl sulfosuccinate
cmc: 2.3 mmole/l
Rejection rate: 30%

Surfactant S2
Sodium dodecylsulfate
cmc: 1.7 mmole/l
Rejection rate: 25%

Surfactant S3
Diisobutylnaphthalenesulfonic acid
cmc: 1.0 mmole/l
Rejection rate: 35%

Surfactant S4

$$R-CH_2-\underset{\underset{OH}{|}}{CH}-(CH_2)_n-SO_3Na$$

$$R-CH=CH-(CH_2)_n-SO_3Na$$

R: C13 alkyl
Hydroxylation ratio: 29.6 mol %
MW: 292 cmc: 0.9 mmole/l
Rejection rate: 45%

Surfactant S5

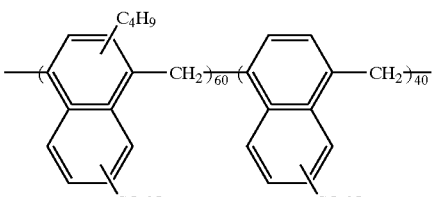

MW: 3,100 cmc: 9.4 μmole/l
Rejection rate: 100%

Surfactant S6

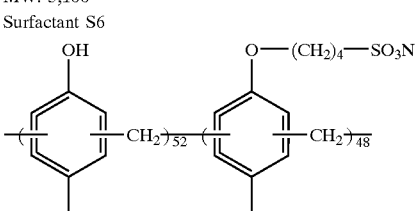

MW 2,240 cmc: 4.5 μmole/l
Rejection rate: 100%

Surfactant S7
Triisopropylnaphthalenesulfonic acid
cmc: 3.7 mmole/l
Rejection rate: 40%

Surfactant S8

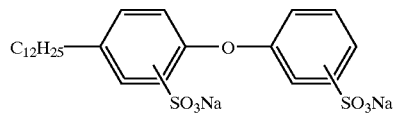

cmc: 1.9 mmole/l
Rejection rate: 42%

The preparation conditions of Organic acid silver salt dispersions 3-A to 3-O are summarized in Table 3.

diameter of 0.42 μm and the maximum particle size of 2.0 μm or shorter. The obtained reducing agent dispersion was

TABLE 3

| Dispersion | Preparation method | Dispersing agent during grain formation |  |  | UF supple- mentation (mM/L) | Dispersing agent during ultrafiltration |  |  | Constant volume dilution |
|---|---|---|---|---|---|---|---|---|---|
|  |  | Kind | Concentration (mM/L) | Addition time |  | Kind | Concentration (wt %/ dispersoid) | Addition time |  |
| 3-A (Comparative) | Crystallization + dispersion (PVA) |  |  |  |  |  |  |  |  |
| 3-B (Inventive) | Crystallization + ultrafiltration | S1 | 45 | Before crystallization |  | PVA | 10 | Immediately after crystallization |  |
| 3-C (Inventive) | Crystallization + ultrafiltration | S2 | 55 | Before crystallization |  | PVA | 10 | Immediately after crystallization |  |
| 3-D (Inventive) | Crystallization + ultrafiltration | S3 | 65 | Before crystallization |  | PVA | 10 | Immediately after crystallization |  |
| 3-E (Inventive) | Crystallization + ultrafiltration | S3 | 65 | Immediately after crystallization |  | PVA | 10 | Immediately after crystallization |  |
| 3-F (Inventive) | Crystallization + ultrafiltration | S4 | 65 | Before crystallization |  | PVA | 10 | Immediately after crystallization |  |
| 3-G (Comparative) | Crystallization + ultrafiltration | PVA | About 0.5 | Before crystallization |  |  |  |  |  |
| 3-H (Comparative) | Crystallization + ultrafiltration | S5 | 0.5 | Before crystallization |  |  |  |  |  |
| 3-I (Comparative) | Crystallization + ultrafiltration | S6 | 0.5 | Before crystallization |  |  |  |  |  |
| 3-J (Inventive) | Crystallization + ultrafiltration | S4 | 65 | Immediately after crystallization | S1 @ 45 | PVA | 10 | @ 2000 μS/cm | × 5 |
| 3-K (Inventive) | Crystallization + ultrafiltration | S7 | 65 | Immediately after crystallization |  | PVP | 10 | Immediately after crystallization |  |
| 3-L (Inventive) | Crystallization + ultrafiltration | S7 | 65 | Immediately after crystallization |  | HEC | 10 | Immediately after crystallization |  |
| 3-M (Comparative) | Crystallization + ultrafiltration | S1 | 45 | Before crystallization | S1 @ 45 |  |  |  |  |
| 3-N (Comparative) | Crystallization + ultrafiltration | S2 | 55 | Before crystallization | S1 @ 55 |  |  |  |  |
| 3-O (Comparative) | Crystallization + ultrafiltration | S3 | 65 | Before crystallization | S1 @ 65 |  |  |  |  |

PVA: Polyvinyl alcohol,
PVP: Polyvinylpyrrolidone,
HEC: Hydroxyethylcellulose
S1 @ 45 means that 45 mM/L of Surfactant S1 was added.
@ 2000 μS/cm means time when conductivity below 2000 μS/cm is attained.

(Preparation of 25 Weight % Dispersion of Reducing Agent)

10 kg of 1,1-bis(2-hydroxy-3,5-dimethylphenyl)-3,5,5-trimethylhexane and 10 kg of a 20 weight % aqueous solution of denatured polyvinyl alcohol (Poval MP203, manufactured by KURARAY CO., LTD.) were added with 16 kg of water, and mixed sufficiently to form a slurry. The slurry was fed by a diaphragm pump to a sand mill of horizontal type (UVM-2, manufactured by Imex Co.) containing zirconia beads having a mean diameter of 0.5 mm, and dispersed for 3 hours and 30 minutes. Then, the slurry was added with 0.2 g of benzothiazolinone sodium salt and water so that the concentration of the reducing agent should become 25% by weight to obtain a reducing agent dispersion. The reducing agent particles contained in the reducing agent dispersion obtained as described above had a median filtered through a polypropylene filter having a pore size of 10.0 μm to remove dusts and so forth, and stored.

(Preparation of 10 Weight % Dispersion of Mercapto Compound)

5 kg of 1-phenyl-2-heptyl-5-mercapto-1,3,4-triazole and 5 kg of a 20 weight % aqueous solution of denatured polyvinyl alcohol (Poval MP203, manufactured by KURARAY CO., LTD.) were added with 8.3 kg of water, and mixed sufficiently to form a slurry. The slurry was fed by a diaphragm pump to a sand mill of horizontal type (UVM-2, manufactured by Imex Co.) containing zirconia beads having a mean diameter of 0.5 mm, and dispersed for 7 6 hours. Then, the slurry was added with water to adjust the concentration of the mercapto compound to 10 weight % in order to obtain a mercapto compound dispersion. The mercapto compound particles contained in the mercapto compound dispersion obtained as described above had a median diameter of 0.40 μm and the maximum particle size of 2.0 μm or less. The mercapto compound dispersion was filtered through a polypropylene filter having a pore size of 10.0 μm to remove dusts and so forth, and stored. The dispersion was filtered through a polypropylene filter having a pore size of 10.0 μm immediately before use.

(Preparation of 20 Weight % Dispersion of Organic Polyhalogenated Compound 1)

5 kg of tribromomethylnaphthylsulfone, 2.5 kg of a 20 weight % aqueous solution of denatured polyvinyl alcohol (Poval MP203, manufactured by KURARAY CO., LTD.) and 213 g of 20 weight % aqueous solution of sodium trusopropylnaphthalenesulfonate were added with 10 kg of water, and mixed sufficiently to form slurry. The slurry was fed by a diaphragm pump to a horizontal type sand mill (UVM-2, manufactured by Imex Co.) which contained zirconia beads having a mean diameter of 0.5 mm, and dispersed for 5 hours. Then, the slurry was added with 0.2 g of benzisothiazolinone sodium salt and water to adjust the concentration of the organic polyhalogenated compound to 20 weight % in order to obtain an organic polyhalogenated compound dispersion. The organic polyhalogenated compound particles contained in the polyhalogenated compound dispersion obtained as described above had a median diameter of 0.36 μm and the maximum particle size of 2.0 μm or less. The obtained organic polyhalogenated compound dispersion was filtered through a polypropylene filter having a pore size of 3.0 μm to remove insoluble solids such as dusts, and then stored.

(Preparation of 25 Weight % Dispersion of Organic Polyhalogenated Compound 2)

A dispersion was prepared in the same manner as the preparation of the 20 weight % dispersion of organic polyhalogenated compound 1 except that 5 kg of tribromomethyl (4-(2,4,6-trimethylphenylsulfonyl)phenyl)sulfone was used instead of 5 kg of tribromomethylnaphthylsulfone, diluted to adjust the concentration of the organic polyhalogenated compound to 25 weight %, and then filtered. The organic polyhalogenated compound particles contained in the organic polyhalogenated compound dispersion obtained as described above had a median diameter of 0.38 μm and the maximum particle size of 2.0 μm or less. The obtained organic polyhalogenated compound dispersion was filtered through a polypropylene filter having a pore size of 3.0 μm to remove insoluble solids such as dusts, and then stored.

(Preparation of 30 Weight % Dispersion of Organic Polyhalogenated Compound 3)

A dispersion was prepared in the same manner as the preparation of the 20 weight % dispersion of organic poly-halogenated compound 1 except that 5 kg of tribromomethylphenylsulfone was used instead of 5 kg of tribromomethylnaphthylsulfone and the amount of the 20 weight % aqueous solution of MP203 was changed to 5 kg, diluted to adjust the concentration of the organic polyhalogenated compound to 30 weight %, and then filtered. The organic polyhalogenated compound particles contained in the organic polyhalogenated compound dispersion obtained as described above had a median diameter of 0.41 μm and the maximum particle size of 2.0 μm or less. The obtained organic polyhalogenated compound dispersion was filtered through a polypropylene filter having a pore size of 3.0 μm to remove dusts and so forth, and stored.

(Preparation of 5 Weight % Solution of Phthalazine Compound)

8 kg of denatured polyvinyl alcohol (Poval MP-203, manufactured by KURARAY CO., LTD.) was dissolved in, 174.57 kg of water and then added with 3.15 kg of 20 weight % aqueous solution of sodium triisopropylnaphthalenesulfonate and 14.28 kg of 70% by weight of 6-isopropylphthalazine was added to obtain a 5 weight % solution of 6-isopropylphthalazine.

(Preparation of 20 Weight % Dispersion of Pigment)

64 g of C.I. Pigment Blue 60 and 6.4 g of Demor N manufactured by Kao Corporation were added with 250 g of water and mixed sufficiently to provide slurry. Then, 800 g of zirconia beads having a mean diameter of 0.5 mm were placed in a vessel together with the slurry and the slurry was dispersed by a dispersing machine (¼ G Sand Grinder Mill; manufactured by Imex Co.) for 25 hours to obtain a pigment dispersion. The pigment particles contained in the pigment dispersion obtained as described above had a mean particle size of 0.21 μm.

(Preparation of 40 Weight % SBR Latex)

An SBR latex purified by ultrafiltration (UF) was obtained as follows.

The SBR latex mentioned below diluted by 10 times with distilled water was diluted and purified by using an UF-purification module FS03-FC-FUYO3A1 (manufactured by Daisen Membrane System K. K.) until the ion conductivity became 1.5 mS/cm, and added with Sandet-BL (manufactured by SANYO CHEMICAL INDUSTRIES, LTD.) to a concentration of 0.22% by weight. Further, the latex was added with NaOH and $NH_4OH$ to adjust the ratio $Na^+$ ion:$NH_4^+$ ion to 1:2.3 (molar ratio) and pH to 8.4. At this point, the concentration of the latex was 40% by weight.

[SBR latex: a latex of -St(68)-Bu(29)-AA(3)-]

The latex had the following characteristics: mean particle size of 0.1 μm, equilibrium moisture of 0.6% by weight content at 25° C., relative humidity 60%, and ion conductivity of 4.2 mS/cm (measured for the latex stock solution (40%) at 25° C. by using a conductometer, CM-30S, manufactured by Toa Electronics, Ltd.).

(Preparation of Coating Solution for Emulsion Layer (Image-forming Layer))

103 g of each of Organic acid silver salt dispersions 3-A to 3-O obtained above, 1.1 g of the 20 weight % aqueous dispersion of the pigment, 5 g of the 20 weight % aqueous solution of polyvinyl alcohol, PVA-205 (manufactured by KURARAY CO. LTD.), 25 g of the 25 weight % dispersion of the reducing agent, 16.3 g in total of Organic polyhalogenated compound dispersions 1, 2 and 3 (weight ratio= 5:1:3), 6.2 g of the 10% mercapto compound dispersion, 106 g of the 40 weight % SBR latex purified by ultrafiltration (UF) and undergone pH adjustment, and 18 ml of the 5 weight % solution of the phthalazine compound were combined, added with 10 g of Silver halide emulsion A, and mixed sufficiently to prepare each of Coating solutions for an emulsion layer 3-A to 3-O. Each coating solution was fed as it was to a coating die in such a feeding amount giving a coating amount of 70 ml/m² and coated.

(Preparation of Coating Solution for Intermediate Layer for Emulsion Surface)

772 g of an aqueous solution of 10% by weight polyvinyl alcohol, PVA-205 (manufactured by KURARAY CO., LTD.), 5.3 g of the 20 weight % dispersion of the pigment, and 226 g of a 27.5 weight % latex of methyl methacrylate/ styrene/butyl acrylate/hydroxyethyl methacrylate/acrylic acid copolymer (copolymerization ratio (by weight): 64/9/ 20/5/2) were added with 2 ml of a 5 weight % aqueous solution of Aerosol OT (manufactured by American Cyanamid Company), 10.5 ml of a 20 weight % aqueous solution of phthalic acid diammonium salt and water in such an amount that gave a total amount of 880 g to form a coating solution for protection and stress prevention layer. This coating solution was fed to a coating die in such an amount that gave a coating amount of 10 ml/m².

The viscosity of the coating solution measured by a B-type viscometer at 40° C. (Rotor No. 1, 60 rpm) was 21 [mPa·s].

(Preparation of Coating Solution for 1st Protective Layer on Emulsion Layer Surface)

64 g of inert gelatin was dissolved in water, added with 80 g of a 27.5 weight % latex solution of methyl methacrylate/styrene/butyl acrylate/hydroxyethyl methacrylate/acrylic acid copolymer (copolymerization ratio (by weight): 64/9/20/5/2), 23 ml of a 10 weight % methanol solution of phthalic acid, 23 ml of a 10 weight % aqueous solution of 4-methylphthalic,acid, 28 ml of 1 N sulfuric acid, 5 ml of a 5 weight % aqueous solution of Aerosol OT (manufactured by American Cyanamid Company), 0.5 g of phenoxyethanol, 0.1 g of benzoisothiazolinone, and water in such an amount that gave a total amount of 750 g to form a coating solution. The coating solution was mixed with 26 ml of 4 weight % chromium alum by a static mixer immediately before coating, and fed to a coating die in such an amount that gave a coating amount of 18.6 ml/m².

The viscosity of the coating solution measured by a B-type viscometer (Rotor No. 1, 60 rpm) at 40° C. was 17 [mPa·s].

(Preparation of Coating Solution for 2nd Protective Layer on Emulsion Layer Surface)

80 g of inert gelatin was dissolved in water, added with 102 g of a 27.5 weight % latex solution of methyl methacrylate/styrene/butyl acrylatethydroxyethyl methacrylate/acrylic acid copolymer (copolymerization ratio (by weight): 64/9/20/5/2), 3.2 ml of a 5 weight % solution of N-perfluorooctylsulfonyl-N-propylalanine potassium salt, 32 ml of a 2 weight % aqueous solution of polyethylene glycol mono(N-perfluorooctylsulfonyl-N-propyl-2-aminoethyl) ether [average polymerization degree of ethylene oxide=15], 23 ml of a 5 weight % aqueous solution of Aerosol TO (manufactured by American Cyanamid Company), 4 g of polymethyl methacrylate micropar- ticles (mean particle size: 0.7 μm), 21 g of polymethyl methacrylate microparticles (mean particle size: 6.4 μm), 1.6 g of 4-methylphthalic acid, 4.8 g of phthalic acid, 44 ml of 1 N sulfuric acid, 10 mg of benzoisothiazolinone and water in such an amount that gave a total amount of 650 g. The mixture was further mixed with 445 ml of an aqueous solution containing 4 weight % chromium alum and 0.67% by weight of phthalic acid by a static,mixer immediately before coating to form a coating solution for surface protective layer, which was fed to a coating die in such an amount that gave a coating amount of 8.3 ml/m².

The viscosity of the coating solution measured by a B-type viscometer (Rotor No. 1, 60 rpm) at 40° C. was 9 [mPa·s].

(Preparation of Photothermographic Material)

On the back side of the aforementioned support having an undercoat layer, the coating solution for antihalation: layer and the coating solution for back surface protective layer were simultaneously applied as stacked layers so as to achieve that the applied solid content amount of the solid microparticle dye in the antihalation layer was 0.04 g/m², and the applied amount of gelatin in the protective layer was 1.7 g/m², and then dried to form an antihalation back layer.

On the side opposite to the back side, an emulsion layer (coated silver amount of the silver halide was 0.14 g/m²), intermediate layer, first protective layer, and second protective layer were simultaneously applied in this order from the undercoat layer by the slide bead application method as stacked layers to form a sample of photothermographic material.

The coating was performed at a speed of 100 m/min. The gap between the tip of coating die and the support was set to be 0.10 to 0.30 mm. The pressure in the reduced pressure chamber was adjusted to be lower than the atmospheric pressure by 196 to 882 Pa. In the subsequent chilling zone, the material was blown with air showing a dry-bulb temperature of, 10 to 20° C. to cool the coating solutions. Then, in the floating type drying zone in a coiled shape, the material was blown with drying air showing a dry-bulb temperature of 23 to 45° C. and a wet-bulb temperature of 15 to 21° C. Subsequently, the material was passed through a drying zone of 70° C. for 20 seconds, and then another drying zone of 90° C. for 10 seconds, and cooled to 25° C.

The prepared photothermographic material showed matting degrees of 550 seconds for the photosensitive layer side, and 130 seconds for the back surface in terms of Beck's smoothness.

Spectral sensitizing dye A

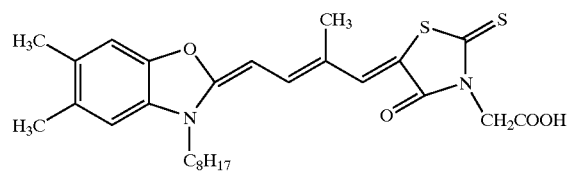

Tellurium sensitizer B

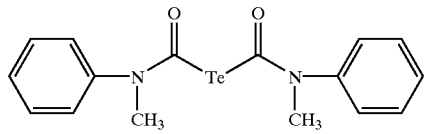

Base precursor compound 11

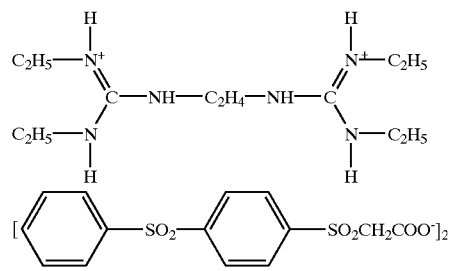

Cyanine dye compound 13

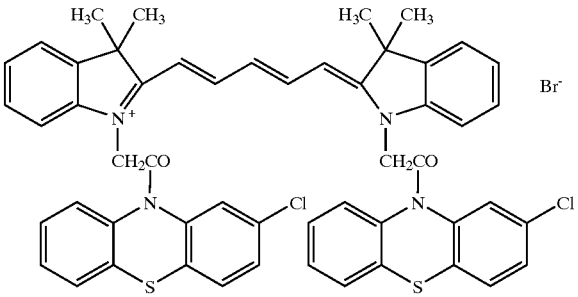

Blue dye compound 14

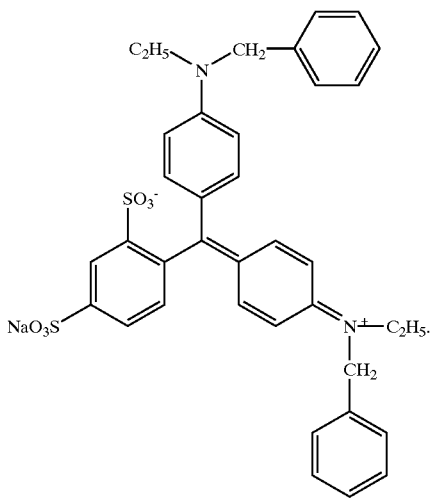

(Evaluation of Photographic Performance)

Each photothermographic material was light-exposed and heat-developed (at about 120° C.) by using Fuji Medical Dry Laser Imager FM-DPL (equipped with a semiconductor laser of 660 nm and a maximum output of 60 mW (IIIB)), and the obtained image was evaluated by a densitometer. The performance was evaluated in terms of Dmin, Dmax and sensitivity as the measurement results, which are shown in Table 4. The sensitivity was evaluated as a reciprocal of a ratio of exposure amounts giving a density higher than Dmin by 1.0, and shown as a relative value based on the sensitivity obtained for Sample A, which was defined as 100.

(Evaluation of Storability After Forced Time Lapse)

Each of the photographic photosensitive materials A to O was cut into a piece of 30.5 cm×25.4 cm, of which corners were cut into round corners having a radius of 0.5 cm, and left under conditions of 25° C. and relative humidity of 50% for 1 days. Ten sheets of each photographic photosensitive material were sealed into a bag made of a moisture-proof material, and the bag was put into a fancy box of 35.1 cm×26.9 cm×3.0 cm, and left at 50° C. for 5 days (forced aging test). The above sample and another sample, which was treated in the same manner as the forced aging test except that the sample was stored at 4° C. for comparison, were subjected to the same treatment as used in the evaluation of photographic performance, and concentrations in fogged areas were measured. The storability after aging was evaluated in terms of fog increase ratio.

Fog increase ratio=[{(Fog of sample subjected to forced aging)−(Fog of comparative sample)}/{(Maximum concentration of comparative sample)−(Concentration of support)}]×100

A lower fog increase ratio indicates better storability after aging.

(Image Storability After Light Irradiation)

A sample subjected to light exposure and development in the same manner as in the evaluation of the photographic performance was adhered to an inside surface of a glass window that was directly irradiated with sun light and left for 1 month. Then, condition of image was evaluated in accordance with the following criteria.

⊚: Substantially no change

○: Slight color change, but negligible

Δ: Color change in image area, but practically acceptable

X: Color change in Dmin and increased concentration

The fog increase ratios and image storability after light irradiation are also shown in Table 4.

TABLE 4

| Dispersion and photothermographic material | Dispersing agent during grain formation | | | | Photographic performance | | | | |
|---|---|---|---|---|---|---|---|---|---|
| | Shape of grain | Average grain diameter (μm) | Variation coefficient (%) | Viscosity (mPa · S) | Dmin | Relative sensitivity | Dmax | Fog increase ratio | Image storability after light irradiation |
| 3-A (Comparative) | Scaly | 0.62 | 16 | 18 | 0.21 | 100 | 3.50 | 5 | ○ |
| 3-B (Inventive) | Acicular | 0.27 | 12 | 39 | 0.21 | 104 | 3.72 | 7 | ○ |
| 3-C (Inventive) | Acicular | 0.32 | 12 | 32 | 0.19 | 103 | 3.69 | 7 | ○ |
| 3-D (Inventive) | Acicular | 0.39 | 16 | 30 | 0.19 | 103 | 3.64 | 3 | ⊚ |
| 3-E (Inventive) | Scaly | 0.47 | 22 | 24 | 0.23 | 102 | 3.58 | 3 | ⊚ |
| 3-F (Inventive) | Tabular | 0.34 | 14 | 46 | 0.20 | 104 | 3.62 | 6 | ○ |
| 3-G (Comparative) | Scaly | 6.09 | Aggregation | 3 | Evaluation was impossible due to bad surface condition | | | | |
| 3-H (Comparative) | Scaly | 1.64 | Aggregation | 8 | | | | | |
| 3-I (Comparative) | Scaly | 2.32 | Aggregation | 4 | | | | | |
| 3-J (Inventive) | Tabular | 0.34 | 18 | 29 | 0.18 | 104 | 3.62 | 4 | ○ |
| 3-K (Inventive) | Scaly | 0.63 | 19 | 18 | 0.19 | 100 | 3.48 | 4 | ⊚ |
| 3-L (Inventive) | Scaly | 0.59 | 21 | 27 | 0.19 | 100 | 3.49 | 4 | ⊚ |
| 3-M (Comparative) | Acicular | 0.27 | 27 | 13 | 0.32 | 56 | 2.56 | 58 | X |

TABLE 4-continued

| Dispersion and photothermographic material | Dispersing agent during grain formation | | | | Photographic performance | | | | |
|---|---|---|---|---|---|---|---|---|---|
| | Shape of grain | Average grain diameter (μm) | Variation coefficient (%) | Viscosity (mPa · S) | Dmin | Relative sensitivity | Dmax | Fog increase ratio | Image storability after light irradiation |
| 3-N (Comparative) | Acicular | 0.31 | 17 | 11 | 0.28 | 39 | 2.68 | 38 | X |
| 3-O (Comparative) | Acicular | 0.40 | 21 | 14 | 0.23 | 48 | 2.75 | 22 | X |

The comparative examples 3-G to 3-I, in which silver behenate grains were prepared by using Surfactants S5, S6 or PVA having a hydrophobic group with 40 or more carbon atoms, provided dispersions in which primary grains markedly aggregated, and photothermographic materials prepared by coating and drying the samples provided high degree of haze and degraded coated surface condition. Therefore, no sample was obtained which was suitable for accurate evaluation of photographic performance by light exposure and measurement of concentration.

Further, in the comparative examples M to O, where surfactants having a hydrophobic group with 8 to 40 carbon atoms, i.e., Surfactants S1, S2 and S3, were used, but the surfactants were not replaced with a nonionic macromolecular surfactant during the ultrafiltration, Dmin became high, whist sensitivity and Dmax decreased, and the problems concerning the fog increase ratio and degradation of image storability after light irradiation became marked.

Contrary to the above comparative examples, it can be understood that the samples 3-B to 3-F and 3-J to 3-L, which were embodiments of the present invention, exhibited photographic performance equivalent to or higher than that of the conventional sample A with respect to Dmin, relative sensitivity, Dmax, fog increase ratio, and image storability after light irradiation.

What is claimed is:

1. A method of producing a silver salt of an organic acid, which comprises:
    (1) reacting, a solution containing silver ions in water or in a mixture of an organic solvent and water, with a solution or suspension containing an alkali metal salt of an organic acid in water, in a mixture of an organic solvent and water, or in an organic solvent to produce a silver salt of an organic acid, and
    (2) removing salt byproduct by a desalting step comprising ultrafiltration,
        wherein a surfactant having a molecular weight of 3000 or less is present during a time period of from before step (1) to before said desalting step (2), and
        adding a dispersing agent having a molecular weight of more than 3000 after completion of the reaction to form the silver salt of an organic acid in step (1) and before completion of the desalting step (2).

2. The method according to claim 1, wherein said dispersing agent having a molecular weight of more than 3000 which is added after completion of the reaction to form the silver salt of an organic acid in step; (1) and before completion of the desalting in step (2) is a nonionic surfactant.

3. The method according to claim 2, wherein a nonionic macromolecular dispersing agent is added after the ultrafiltration step is performed, and the conductivity of the organic acid silver salt dispersion is less than 2000 μS/cm at the time of or during the addition of the nonionic macromolecular dispersing agent.

4. The method according to claim 3, wherein 2- to 10-fold constant volume dilution is performed after the addition of the nonionic macromolecular dispersing agent.

5. The method according to claim 2, wherein the nonionic dispersing agent is a nonionic macromolecular dispersing agent introduced during the ultrafiltration having a concentration of 0.1 to 30% by weight of the solid content of the silver salt of an organic acid.

6. The method according to claim 2, wherein the dispersing agent introduced during the ultrafiltration is a nonionic macromolecular dispersing agent selected from the group consisting of polyvinyl alcohol, polyvinylpyrrolidone, hydroxypropylcellulose, and a combination thereof.

7. The method according to claim 1, wherein the surfactant having a molecular weight of 3000 or less is an ionic surfactant that has anionic properties and has at least one hydrophobic group having 8 to 40 carbon atoms.

8. The method according to claim 7, wherein the desalting step (2) is carried out by ultrafiltration which employs an ultrafiltration membrane having a fractional molecular weight 10 to 50 times as much as the molecular weight of the ionic surfactant.

9. The method according to claim 8, wherein the dispersing agent having a molecular weight of more than 3000 has a molecular weight 5 to 50 times as much as the fractional molecular weight of the ultrafiltration membrane.

10. The method according to claim 7, wherein the desalting step (2) is carried out by ultrafiltration which employs an ultrafiltration membrane having 0 to 50% of rejection against the ionic surfactant.

11. The method according to claim 7, wherein a concentration of the ionic surfactant present in the reaction mixture is 5 to 100 times the critical micelle concentration of surfactant.

12. The method according to claim 7, wherein the ionic surfactant is added before completion of the addition of the solution containing silver ions.

13. The method according to claim 7, wherein the ionic surfactant introduced into the reaction mixture has at least-one hydrophilic group selected from the group consisting of sulfonic acid salt or sulfuric acid ester salt, and wherein said surfactant has at least one aromatic group.

14. The method according to claim 7, wherein the ionic surfactant concentration is maintained constant by addition of the same surfactant as the ionic surfactant present during the time the byproduct salt is removed by ultrafiltration.

15. The method according to claim 7, wherein the ionic surfactant concentration is maintained constant by addition of a surfactant different from the ionic surfactant present during the time the byproduct salt is removed by ultrafiltration.

16. The method according to claim 1, wherein 2 to 20-fold constant volume dilution is performed after the addition of the dispersing agent, and then the dispersion is concentrated to a concentration of 10% to 50%. by weight.

17. The method according to claim 1, wherein said surfactant is selected from the group consisting of an anionic surfactant and a cationic surfactant.

* * * * *